(12) United States Patent
Katz et al.

(10) Patent No.: US 12,380,987 B2
(45) Date of Patent: *Aug. 5, 2025

(54) DIET MAPPING PROCESSES AND SYSTEMS TO OPTIMIZE DIET QUALITY AND/OR MINIMIZE ENVIRONMENTAL IMPACT

(71) Applicant: Diet ID, Inc., Detroit, MI (US)

(72) Inventors: David L. Katz, Hamden, CT (US); Lauren Q. Rhee, Fulton, MD (US)

(73) Assignee: Diet ID, Inc., Detroit, MI (US)

( * ) Notice: Subject to any disclaimer, the term of this patent is extended or adjusted under 35 U.S.C. 154(b) by 366 days.

This patent is subject to a terminal disclaimer.

(21) Appl. No.: 17/739,593

(22) Filed: May 9, 2022

(65) Prior Publication Data

US 2022/0328163 A1    Oct. 13, 2022

Related U.S. Application Data

(63) Continuation-in-part of application No. 16/614,675, filed as application No. PCT/US2018/033443 on May 18, 2018, now Pat. No. 11,328,810.

(60) Provisional application No. 62/635,242, filed on Feb. 26, 2018, provisional application No. 62/508,613, filed on May 19, 2017.

(51) Int. Cl.
*G16H 20/60* (2018.01)

(52) U.S. Cl.
CPC ................... *G16H 20/60* (2018.01)

(58) Field of Classification Search
CPC ....................................................... G16H 20/60
See application file for complete search history.

(56) References Cited

U.S. PATENT DOCUMENTS

| 5,454,721 A | 10/1995 | Kuch |
| 6,553,386 B1 | 4/2003 | Alabaster |

(Continued)

FOREIGN PATENT DOCUMENTS

| TW | 201601089 A | 1/2016 |
| WO | 2016079719 A1 | 5/2016 |

OTHER PUBLICATIONS

International Search Report and Written Opinion from related International Patent Application No. PCT/US2019-067909 issued Mar. 25, 2020.

(Continued)

*Primary Examiner* — Aryan E Weisenfeld
(74) *Attorney, Agent, or Firm* — McCarter & English, LLP

(57) ABSTRACT

A computer infrastructure operable to implement: a) a diet identification tool configured to identify qualities of a diet of a user on a graphical user interface based on composite images selected by the user; and a composite image tool, wherein the composite image tool is populated with a library of composite images, wherein each composite image comprises an inventory of foods in specific portions, wherein each image depicts relative proportions of ingredients, dishes and meals representative of a particular diet and wherein the composite images are accessed through the graphical user interface and a computer program product comprising a computer usable medium having readable program code embodied in the medium, the computer program product including at least one component that when executed by a processor is operable to provide an assessment of a personalized diet type and quality of a user based on imputed information.

10 Claims, 19 Drawing Sheets

ILLUSTRATION: DIET TYPES ARE LETTERED; DIET QUALITY IS NUMBERED. DIET TYPE C HAS ENTRIES AT ALL LEVELS OF QUALITY, AND THUS FOR THAT DIET TYPE, THE HIGHEST AND LOWEST QUALITY ENTRIES ARE 'TRUE TO TYPE.' DIET TYPE A HAS ONLY HIGH QUALITY ENTRIES; FOR LOWER QUALITY CHOICES, REVERT FIRST TO B, THEN C. DIET TYPE D HAS ONLY LOW-QUALITY VARIANTS; FOR HIGHER QUALITY CHOICES, REVERT TO C. DIET TYPE E ALSO HAS ONLY LOW QUALITY VARIANTS; FOR HIGHER QUALITY CHOICES, REVERT FIRST TO D, THEN C.

|  | LOW | ← | DIET QUALITY | | | → | HIGH | |
|---|---|---|---|---|---|---|---|---|
| DIET TYPES | A1 | A2 | A3 | A4 | A5 | A6 | A7 | A8 |
| | B1 | B2 | B3 | B4 | B5 | B6 | B7 | B8 |
| | C1 | C2 | C3 | C4 | C5 | C6 | C7 | C8 |
| | D1 | D2 | D3 | D4 | D5 | D6 | D7 | D8 |
| | E1 | E2 | E3 | E4 | E5 | E6 | E7 | E8 |

(56) References Cited

U.S. PATENT DOCUMENTS

| | | |
|---|---|---|
| 6,585,516 B1 | 7/2003 | Alabaster |
| 7,558,788 B1 | 7/2009 | Herdman |
| 8,738,432 B2 | 5/2014 | Hamilton, II et al. |
| 8,777,624 B2 | 7/2014 | Klein |
| 9,110,553 B2 | 8/2015 | Ash et al. |
| 9,449,029 B2 | 9/2016 | Ting et al. |
| 9,892,501 B2 | 2/2018 | Dehais et al. |
| 2001/0000810 A1 | 5/2001 | Alabaster |
| 2002/0047867 A1 | 4/2002 | Mault et al. |
| 2003/0059747 A1 | 3/2003 | Yoshida et al. |
| 2003/0182160 A1 | 9/2003 | Lahteenmaki |
| 2008/0275729 A1 | 11/2008 | Taggart et al. |
| 2010/0080875 A1 | 4/2010 | Miller-Kovach et al. |
| 2011/0318717 A1 | 12/2011 | Adamowicz |
| 2012/0190386 A1 | 7/2012 | Anderson |
| 2013/0027424 A1 | 1/2013 | Mochizuki |
| 2013/0085345 A1 | 4/2013 | Geisner et al. |
| 2013/0108993 A1 | 5/2013 | Katz |
| 2015/0205502 A1 | 7/2015 | Ubillos et al. |
| 2015/0347520 A1 | 12/2015 | King et al. |
| 2016/0035248 A1 | 2/2016 | Gibbs |
| 2016/0351072 A1 | 12/2016 | Nusbaum et al. |
| 2017/0128007 A1 | 5/2017 | Hayter et al. |
| 2017/0243513 A1 | 8/2017 | Katz |
| 2018/0267683 A1 | 9/2018 | Tessier et al. |

OTHER PUBLICATIONS

Biltoft-Jensen-Jensen, A. et al., "Diet quality: associations with health messages included in the Danish Dietary 3uidelines 2005, personal attitudes and social factors," Public Health Nutrition, vol. 12, No. 8, pp. 1165-1173 (Sep. 15, 2008).

Guenther, P. et al., Update of the Healthy Eating Index: HEI-2010, J. Acad. Nutr. Diet, pp. 1-21 (Feb. 2013).

Guenther, P. et al., Update of the Healthy Eating Index: HEI-2010, J. Acad. Nutr. Diet, vol. 113, No. 4, pp. 1-20 (Apr. 2013).

Hiza, H. et al., Diet Quality of Children Age 2-17 Years as Measured by the Healthy Eating Index-2010, U.S. Department of Agriculture, Nutrition Insight 52 (Jul. 2013).

Holm, L. et al., "Eating practices and diet quality: a population study of four Nordic countries," European Journal of Clinical Nutrition, vol. 69, pp. 791-798; entire document (Apr. 29, 2015).

Hungry Planet: What The World Eats, Time [Retrieved from the internet on Jun. 2, 2017 at http:/Jworld.time.com/2013/09/20/hungry-planet-what-the-world-eats/photo/nor_ 130523_ 139_x/.] (Sep. 20, 2013).

Katz, D. et al., Can We Say What Diet is Best for Health?, Annu. Rev. Pub. Health, vol. 35, pp. 83-103 (2014).

Kim, S. et al., The Diet Quality Index-International (DQI-1) Provides an Effective Tool for Cross-National Comparison of Diet Quality as Illustrated by China and the United States, Journal of Nutrition, vol. 133, pp. 3476-3484 (2003).

Mailot, M. et al., "To Meet Nutrient Recommendations, Most French Adults Need to Expand Their Habitual Food Repertoire," The Journal of Nutrition, Nutrient Requirements and Optimal Nutrition, pp. 1721-1727 (Jul. 22, 2009).

Malagoli, C. et al., "Diet Quality and Risk of Melanoma in an Italian Population," The Journal of Nutrition, Nutrition and Disease, pp. 1800-1807 (Jun. 24, 2015).

U.S. Appl. No. 17/352,166, filed Jun. 18, 2021, Katz et al.

ILLUSTRATION: DIET TYPES ARE LETTERED; DIET QUALITY IS NUMBERED. DIET TYPE C HAS ENTRIES AT ALL LEVELS OF QUALITY, AND THUS FOR THAT DIET TYPE, THE HIGHEST AND LOWEST QUALITY ENTRIES ARE 'TRUE TO TYPE.' DIET TYPE A HAS ONLY HIGH QUALITY ENTRIES; FOR LOWER QUALITY CHOICES, REVERT FIRST TO B, THEN C. DIET TYPE D HAS ONLY LOW-QUALITY VARIANTS; FOR HIGHER QUALITY CHOICES, REVERT TO C. DIET TYPE E ALSO HAS ONLY LOW QUALITY VARIANTS; FOR HIGHER QUALITY CHOICES, REVERT FIRST TO D, THEN C.

| | LOW | | | ← DIET QUALITY → | | | HIGH | |
|---|---|---|---|---|---|---|---|---|
| DIET TYPES | A1 | A2 | A3 | A4 | A5 | A6 | A7 | A8 |
| | B1 | B2 | B3 | B4 | B5 | B6 | B7 | B8 |
| | C1 | C2 | C3 | C4 | C5 | C6 | C7 | C8 |
| | D1 | D2 | D3 | D4 | D5 | D6 | D7 | D8 |
| | E1 | E2 | E3 | E4 | E5 | E6 | E7 | E8 |

FIG. 1

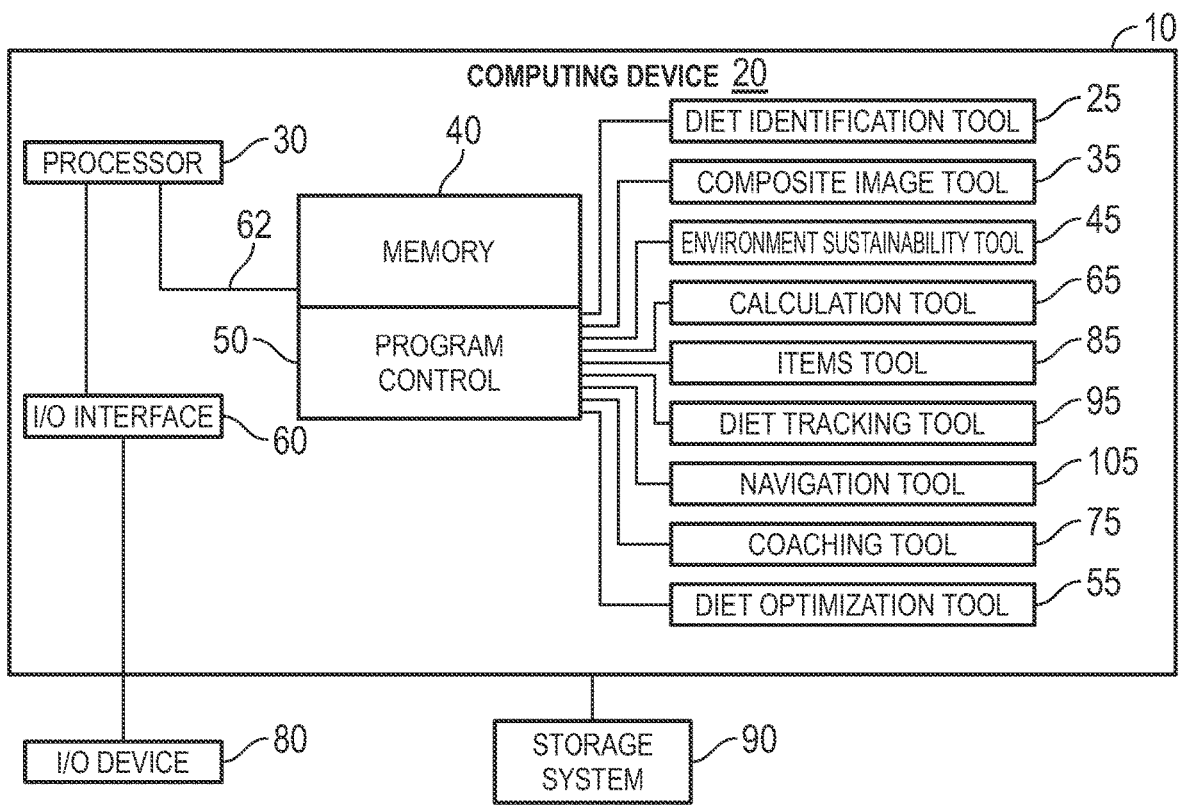

FIG. 2

DIET (ID)

HELP US ID YOUR DIET
TELL US ABOUT YOUR CURRENT DIET.

BACK

DO YOU CURRENTLY FOLLOW ANY PARTICULAR KIND OF DIET?

NEED HELP SELECTING?

| NOTHING IN PARTICULAR | |
|---|---|
| AMERICAN | SOUTHERN |
| FLEXITARIAN | VEGAN |
| LOW-CARB | VEGETARIAN |
| LOW-FAT | MEDITERRANEAN |
| PALEO | PESCATARIAN |

? NEED HELP SELECTING?

DIET (ID)

HELP US ID YOUR DIET
TELL US ABOUT YOUR CURRENT DIET.

BACK

DO YOU CURRENTLY FOLLOW ANY PARTICULAR KIND OF DIET?

NEED HELP SELECTING?

| NOTHING IN PARTICULAR | |
|---|---|
| AMERICAN | SOUTHERN |
| FLEXITARIAN | VEGAN |
| LOW-CRAB | VEGETARIAN |
| LOW-FAT | MEDITERRANEAN |
| PALEO | PESCATARIAN |

NEXT

FIG. 4

DIET ID

HELP US ID YOUR DIET
TELL US ABOUT YOUR CURRENT DIET.

BACK

DO YOU CURRENTLY HAVE ANY DIETARY RESTRICTIONS?

NEED HELP SELECTING?

| I DO NOT HAVE ANY RESTRICTIONS. | |
|---|---|
| DAIRY-FREE | NUT-FREE |
| GLUTEN-FREE | WHEAT-FREE |
| SHELLFISH-FREE | SOY-FREE |
| PEANUT-FREE | ALCOHOL-FREE |
| EGG-FREE | |

? NEED HELP SELECTING?

| | | | |
|---|---|---|---|
| | | YOUR CURRENT SELECTIONS | |
| AMERICAN Q7™ | | MEDITERRANEAN Q8™ | |
| AMERICAN QUALITY 7 (Q7) IS CHARACTERIZED BY SOME FRUITS AND VEGETABLES, MORE WHOLE GRAINS, NUTS AND SEEDS, LOW-FAT DAIRY PRODUCTS, AND LEANER MEALS. | | MEDITERRANEAN QUALITY 8 (Q8) IS CHARACTERIZED BY VEGETABLES, FRUITS, NUTS AND SEEDS, WHOLE GRAINS, LEGUMES, LOW-FAT DAIRY OLIVES, SEAFOOD AND LEAN POULTRY. RED WINE (MODERATION). | |
| UPDATE ID | | UPDATE IDEAL | |
| 2066 KCAL | DAILY CALORIES | 1566 KCAL | -500 KCAL |
| 45% | CARBOHYDRATES | 44% | -7% |
| 16% | TOTAL PROTEIN | 17% | -2% |
| 37% | TOTAL FAT | 36% | -1% |
| 37% | TOTAL SUGARS | 77% | -1% |
| 9% | ADDED SUGARS | 5% | -4% |
| 13% | SATURATED FAT | 15% | -2% |
| 12% | MONOUNSATURATED FAT | 12% | -3% |
| 9% | POLYUNSATURATED FAT | 7% | -2% |
| 3207 mg | SODIUM | 3114 mg | 60 mg |
| 21 g | FIBER | 9 g | -42 g |
| 2 g | OMEGA-3 FAT | 1 g | -1 g |
| 310 mg | CHOLESTEROL | 288 mg | -22 mg |
| 2726 mg | POTASSIUM | 1643 mg | -4083 mg |
| 1139 mg | CALCIUM | 576 mg | -563 mg |
| 319 mg | MAGNESIUM | 183 mg | -38 mg |
| 15 mg | IRON | 12 mg | -1 mg |
| 738 mg | VITAMIN A | 324 mg | -414 mg |
| 60 mg | VITAMIN C | 52 mg | -6 mg |
| 5 mcg | VITAMIN D | 3 mcg | -2 mcg |
| 10 mg | VITAMIN E | 5 mg | -5 mg |

FIG. 36

DIET MAPPING PROCESSES AND SYSTEMS TO OPTIMIZE DIET QUALITY AND/OR MINIMIZE ENVIRONMENTAL IMPACT

RELATED APPLICATIONS

This application is a continuation-in-part of U.S. patent application Ser. No. 16/614,675, filed on Nov. 18, 2019, which claims the benefit of and priority to International Patent Application No. PCT/US2018/033443, filed on May 18, 2018, and which claims the benefit of and priority to U.S. Provisional Application No. 62/635,242, filed on Feb. 26, 2018 and U.S. Provisional Application No. 62/508,613, filed on May 19, 2017, the disclosures of all of the foregoing applications are incorporated by reference herein in their entirety.

FIELD OF THE INVENTION

The present invention relates generally to a method of quantifying health and environmental impacts of various diets and to a computer-based tool for optimizing qualities or characteristics of diet in terms of health and/or environmental sustainability.

BACKGROUND OF THE INVENTION

The global agricultural system is capable of producing enough food to feed everyone on the planet. However, access to and consumption of sufficient food that is nutritious and affordable as well as environmentally sustainable, is not always possible for many families. Population growth projections over the next half century also highlight the need for minimizing adverse environmental impacts and improving the environmental sustainability of our food system.

Good diet quality is a major contributing factor to the health and well-being of individuals and families Global dietary patterns have changed dramatically over time, which is both a benefit and a detriment to the health and well-being of individuals and families Increased income has been accompanied by increased consumption of foods (and diets) with greater quantities of meat, dairy, oil, salt and processed foods. In addition, globalization of food sources has led to environmental degradation and biodiversity loss, while at the same time lowered prices for diets that may satisfy caloric needs but be low in variety and important nutrients. Coupled with urbanization and increased sedentary lifestyles, there has been an unprecedented rise in obesity and, related diseases such as cardiovascular disease, diabetes and hypertension.

The Food and Agriculture Organization of the United Nations (FAO) has defined "sustainable diets" as "those diets with low environmental impacts which contribute to food and nutrition security and to healthy life for present and future generations. Sustainable diets are protective and respectful of biodiversity and ecosystems, culturally acceptable, accessible, economically fair and affordable; nutritionally adequate, safe and healthy; while optimizing natural and human resources." This definition reflects the recognition that the health of individuals cannot be isolated from the health of ecosystems.

Agricultural intensification, poverty, population pressures, urbanization, and lifestyle all contribute to changes in food production, preparation and consumption, all of which can impact diet and in turn health of individuals.

Environmental impacts are one of the major concerns when addressing the sustainability of food product and sustainable food consumption strategies. To assess to what extent food production affects the environment, an environmental assessment tool can be used. Different types of assessment tools have been developed to establish environmental indicators, which can be used to determine the environmental impacts of livestock production systems or agricultural products. These environmental assessment tools can be divided into "area-based" or "product-based" tools.

Area-based indicators include, for example, nitrates leached per hectare from a pig farm and are useful for evaluating farm emissions of nutrients such as nitrates that have an effect on the local environment.

Product-based indicators include, for example, global warming potential (GWP) per kg of meat. Product-based indicators are useful for evaluating the impact of food production on the global environment and have the advantage that, in addition to emissions from the farms, emission related to the production of inputs and outputs are also included. Product-based evaluation is also call life cycle assessment (LCA) and is an approach that evaluates all stages of a product's life. During the evaluation, environmental impacts from each stage are considered from raw material products, processing, distribution, use and disposal. The methodology considers not only the flow of materials, but the outputs and environmental impacts of these. Life cycle analysis processes follow the main steps of goal definition and scoping to define the process and boundaries; inventory analysis to identify material and energy flows and environmental releases; impact assessment to assess the environmental effects of inventory analysis, and interpretation to draw conclusions from the assessment. Conclusions can include decisions on different materials or processes. The benefits of life cycle analysis are that it helps avoid shifting environmental problems from one place to another when considering such decisions.

Ultimately, the life cycle approach for a product is adopted to reduce its cumulative environmental impacts. LCA is done in terms of a functional unit (FU) for a food, meaning a finished product such as a pound of cheese, kilogram of meat or gallon of milk In LCA, all relevant emissions and resources used through the life cycle of a product are aggregated and expressed in terms of FU.

Commonly applied environmental impact categories within LCA of food products include:
1) Global warming potential (GWP);
2) Eutrophication;
3) Acidification;
4) Photochemical smog; and
5) Land use.

For each of the environmental impact categories, emitted substances throughout the product chain that contribute to the environmental impact category can quantified.

Global warming potential (GWP) refers to the addition of greenhouse gases to the atmosphere through the burning of fossil fuels, agricultural practices and certain industrial practices leading to major changes in the earth's climate system. Nitrous oxide, methane and carbon dioxide are some of the most important contributors to global warming. Nitrous oxide is emitted from slurry handling and from fields. Methane is emitted from enteric fermentation, and from manure/slurry handling and storage. Carbon dioxide is emitted from the combustion of fossil fuels (traction, transport, and heating) and can be emitted from the soil if more organic matter is degraded than built up in the soil.

Eutrophication is caused by the addition of excess nutrients to water and results in algal blooms that lower the concentration of dissolved oxygen, thereby killing fish and other organisms.

Acidification is caused by release of acid gases, mostly from the burning of fossil fuels. The major element that contributes to acidification from livestock product is ammonia emitted from manure handling.

For consumers and the food industry, it is important to have knowledge of the environmental impacts of the produced food. For example, the environmental impact of meat includes both the impact from the production of the living animal on the farm, and all the processes after the animal leaves the farm and until the meat arrives at the refrigerated counter in the supermarket.

However, when comparing foods on a weight by weight basis; products are not wholly substitutable and cannot replace each other but rather must be used complementary. There is more protein, for example, in meat and dairy products than in vegetables and a different mix of vitamins. The environmental impact of the individual product must be evaluated in context of how much it contributes to total food consumption of an individual or family. For example, if an individual or family reduces meat consumption, both greenhouse gas emissions and nutrient losses can be reduced. However, the resulting environmental impact will depend on whether the meat is replaced with field-grown vegetables (less environmental impact) or with greenhouse-grown vegetables (greater environmental impact). Thus, it is very difficult for an individual to determine what food choices will have the most positive (or negative) environmental impact and to optimize their diet to minimize environmental effects.

A consumer looking for food in a supermarket may try to evaluate the environmental impacts of a product based on various characteristics and determinants as illustrated in Table 1. In addition, the consumer may also be influenced by other characteristics, including price and taste that are unrelated to environmental impacts.

TABLE I

Determinants of environmental impacts:

| Determinant of environmental impact | Corresponding product characteristics | Features of characteristics |
|---|---|---|
| Type of product and agricultural practice (e.g., greenhouse or organic production) | Product label, season, origin, and product category | Meat or vegetable from greenhouse, organic or other production |
| Processing in food industry and distribution of product | Type of conservation | Fresh, chilled, deep-frozen, pasteurization |
| Distance and mode of transportation | Country or area of origin | Region, overseas |
| Type and amount of packaging materials | Material of packaging | Cardboard, glass, metal, paper, plastic, Styrofoam |
| Cooling, cooking, etc. during consumption | Depending on type of conservation and household behavior | Fresh, chilled, deep-frozen, pasteurized |

In order to evaluate diet quality as it relates to minimizing environmental impacts or on the basis of environmental sustainability, it is necessary to obtain information regarding current dietary intake of the individual and/or household and to evaluate the environmental impacts of the current level of diet quality and/or the current type of diet. Thus, in order to determine if a diet is optimal in terms of minimizing adverse environmental impacts, dietary intake of the individual and/or household must be evaluated and then optimized according to objective criteria of environmental impacts and/or environmental sustainability.

Many consumers tend to be environmentally conscious and desire to make dietary decisions that minimize overall environmental impact. However, it is currently not possible to determine which product may be more "environmentally polluting" or "environmentally advantageous" simply by reading labels and only buying products that are "organic" or "free-range" as these products may or may not be the best choices in terms of environmental sustainability since these labels do not necessarily address sustainability. Thus, it would be desirable to provide an improved method by which a consumer can modify their diet to a more environmentally-friendly or environmentally-sustainable diet in an easy to use format and that is capable of providing feedback to the consumer in making choices that are more environmentally sustainable.

U.S. Pat. No. 8,738,432 to Hamilton, I I et al., the subject matter of which is herein incorporated by reference in its entirety, describes a method and system for segmenting items in an online "shopping cart" according to carbon footprint to promote environmental stewardship. However, this patent merely suggests foods that can be swapped out for other complementary items and does not address the larger issuer of modifying diet to a more environmentally sustainable diet based on various factors.

Foods individuals habitually consume are affected by a number of inter-related factors including, for example, food availability, food accessibility, and food choice which in turn are influenced by geography, demography, income, socio-economic status, urbanization, globalization, religion, culture, marketing, consumer attitude, among others.

Good health, economic development and environmental sustainability are indirectly influenced by agriculture. The effects on employment, income, and economic prosperity are positive because they enable individuals to lead healthier lives, that have less strain on budgets for health care.

Agriculture also affects economic determinants of sustainable diets, and the income amount and distribution of income of a population is a major factor regarding the affordability of a diet. Populations with higher incomes have the ability to purchase foods of greater variety and nutritional value. In addition, nations with high gross domestic products are able to access foods more readily and invest in agricultural practices that not only provide enough foods for their citizens, but more nutritious and diverse foods as well.

Government food and social protection policies can also affect diet access and affordability. For example, farm subsidies can benefit and distort markets and negatively affect health and nutrition, by encouraging the development of large quantities of cheap, stable, and ultra-processed foods that can be less expensive than locally produced and often healthier food options.

Social and cultural norms also play an important role in diets. Diets serve not only to provide nourishment but also to provide pleasure influenced by social traditions. In various countries, the consumption of certain traditional diets has contributed to nutritional deficiencies, affected diet diversity and contributed to increased incidence of diet-related diseases in a population. On the other hand, an individual's knowledge of foods in the diet and their contribution to health and nutrition can lead to the consumption of a more varied and nutritionally adequate diet. Additionally, knowing how to prepare a more varied diet can affect consumption of different food products.

Most countries have adopted dietary recommendations to encourage healthy consumption patterns. However, very few of these dietary recommendations have anything to do with environmental impacts and sustainability.

Co-pending application Ser. No. 15/246,146 to Katz, the subject matter of which is herein incorporated by reference in its entirety, describes a method for capturing baseline diet composition, goal (desired) diet composition, and providing step-by-step guidance from baseline to goal via a customized, preferred "route" experienced by the user. In addition, application Ser. No. 62/508,613 to Katz et al., the subject matter of which is herein incorporated by reference in its entirety, describes methods of quantifying and mapping diet quality.

As described in these co-pending applications, conventional dietary intake measures, including, for example, food frequency questionnaires, food diaries, and dietary recall, are notoriously prone to inaccuracies despite being very labor-intensive. They are, in fact, labor intensive for both the "client" and the professionals (i.e., dietitians, nutrition researchers, etc.) who rely on them for data. Because they are tedious, cumbersome, and not user-friendly, they are ill-suited to consumer-facing applications that are intended to be "inviting" or fun to use, such as apps on smart phones or other wearable technology (e.g. smart watches). In contrast, there are a bounty of fitness applications that can be easily with no cumbersome data entry at the start.

Adapting food choices to meet dietary requirements for health can also aid in mitigating climate change. However, one of the main differences in the approach to recommendations for health and the environment is that dietary recommendations for health are based mainly on nutrient requirements, which can be achieved through many combinations of foods, while dietary impact is generally associated with the reduction or elimination of specific foods, such as meat and dairy, from a diet. However, there are some synergies. For example, a reduction in the intake of meat and dairy products may benefit health because, together, these products contribute to a high intake of saturated fats in many typical diets and a high consumption of red and processed meats has been linked to various cancers. However, any reduction in these foods needs to be considered in the context of the whole diet to ensure that substitutions made in the diet are appropriate for health.

Changing or modifying food intake to address environmental impacts may involve improving food choices to reduce greenhouse gas emissions, as well as the impacts of dietary choices on water use, land use, waste, biodiversity, as well as social, ethical, and economic issues that threaten future food security. However, it is not a simple task for a consumer to optimize their diet for health while at the same time also optimizing their diet for environmental sustainability.

Thus, it would be desirable to develop a computer-based tool to assist a consumer in identifying deficiencies in their diet in terms of environmental sustainability and/or health and in optimizing their diet to a different level of diet or type of diet for sustainability while maintaining a high-quality diet for good overall health. In addition, it would also be desirable to develop methods for quantifying and mapping diet quality in term of overall health and/or environmental sustainability.

SUMMARY OF THE INVENTION

It is an object of the present invention to provide a computer program product and a method of using the same to assess diet type and quality of a user.

It is another object of the present invention to provide a computer-based tool to assist a user in identifying deficiencies in their diet for good overall health.

It is another object of the present invention to provide a computer-based tool to assist a consumer in modifying their diet from a current diet to a more optimal diet for their health.

It is still another object of the present invention to provide a computer-based tool to assist a consumer in modifying their diet to be more environmentally sustainable.

It is still another object of the present invention to provide a computer-based tool that can provide guidance to a consumer in terms of health and/or environmental impacts of their diet.

It is still another object of the present invention to provide an improved method of quantifying and mapping diet quality.

In one embodiment, the present invention relates generally to a system implemented in hardware comprising:
　a computer infrastructure operable to implement:
　　a diet identification tool configured to identify qualities of a diet of a user on a graphical user interface based on composite images selectable by the user; and
　　a composite image tool, wherein the composite image tool is populated with a library of composite images, wherein each composite image depicts a unique inventory of proportions of foods, ingredients, dishes and meals representative of a particular diet quality level X of a particular diet type N for a period of time, and wherein the library of composite images is accessed using the diet identification tool on the graphical user interface, and
　at least one of:
　　1) an environmental sustainability tool to identify an environmental quality of the diet of the user based on composite images selected by the user;
　　2) a diet optimization tool configured to allow the user to select a different diet type N and/or diet quality level X using the composite image tool and the diet identification tool;
　　3) a calculation tool configured to calculate personalized nutrient levels and personalized environmental impacts of the user based on inputted information of the user, wherein the graphical user interface is configured to allow the input of the information and to display the calculated personalized nutrient levels to the user;
　　4) a coaching tool populated with a plurality of coaching tips comprising discrete steps and changes to allow the user to move from one N diet type to a different N diet type and/or from one level of diet quality X to a different level of diet quality X, wherein the graphical user interface is configured to display the coaching tips to the user;
　　5) a diet tracking tool, wherein the diet tracking tool allows the user to change or update their diet type N, change or update their level of diet quality X, and compare changes in level of diet type N and level of diet quality X over time; and wherein the graphical user interface is configured to display the changes; and
　　6) a navigation tool populated with discrete steps to move the user stepwise from one level of diet quality X of one N diet type to a different N diet type and/or from one level of diet quality X to a different level of diet quality X, wherein the graphical user interface is configured to display a navigation route to the user.

In another embodiment, the present invention also relates generally to a computer program product comprising a computer usable medium having readable program code embodied in the medium, the computer program product including at least one component that when executed by a processor is operable to:

A) display a menu of N diet types for selection by a user on a graphical user interface, B) display a first plurality of unique composite images of diet quality levels Xn, wherein each composite image contains images of foods in specific portions and depicts relative portions of ingredients, dishes and meals representative of the level of diet quality Xn of the N diet type selected by the user;

C) display a different plurality of unique composite images of diet quality levels Xn upon selection by the user of one of the unique composite images in the first plurality of unique composite images, wherein one composite image of the level of diet quality Xn is the same as in the display of the first plurality of unique composite images and at least one composite image is different;

D) display an input screen to allow the user to input personal information about the user on the graphical user interface;

E) display an input screen to allow the user to input diet modification information on the graphical user interface; and F) calculate a user specific assessment of diet quality and type for the user and display the calculated user specific assessment of diet quality and type to the user on the graphical user interface.

BRIEF DESCRIPTION OF THE FIGURES

For a fuller understanding of the invention, reference is made to the following description taken in connection with the accompanying figures, in which:

FIG. 1 depicts an illustration of a grid of diet types N and levels of diet quality X.

FIG. 2 depicts a system comprising an environment for managing processes in accordance with one aspect of the present invention.

FIGS. 3-36 depict screen shots of a graphical user interface in accordance with one aspect of the present invention.

DETAILED DESCRIPTION OF THE PREFERRED EMBODIMENTS

Figures 5, 6:
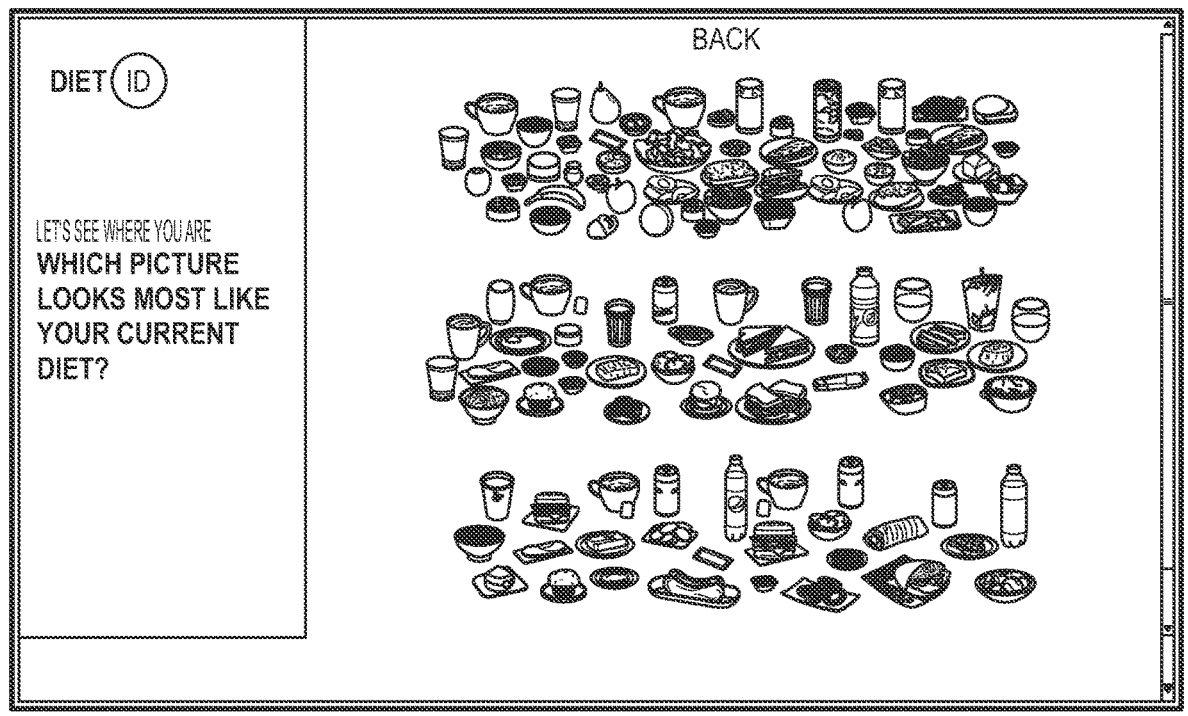

As described in application Ser. No. 15/246,146 to Katz, levels of diet quality can be translated into photographic representations of a dietary pattern, by steps comprising:

a) using a diet quality measure to identify a plurality of dietary patterns that each represent a level of diet quality for a period of time;

b) assigning a dietary score to each of the plurality of dietary patterns;

c) converting the plurality of dietary patterns into representative dietary patterns; and d) converting the representative dietary patterns into composite images, wherein each composite image depicts a photographic representation of the dietary patterns for the period of time.

Thus, using this methodology, a library of composite images can be created in which each composite depicts a unique inventory of proportions of foods, ingredients, dishes, and meals, representative of a particular diet quality level X of a particular diet type N for a period of time.

The dietary patterns may include any of a number of typical dietary patterns for a given population, considering "poor," "good," "better," and "best" diets for the given population. Thus, using this methodology, it is possible to map differences in diets using common coordinates to create desired gradients within those diets.

As also described herein, the inventors of the present invention have determined that unique differences and characteristics of diet in terms of environmental quality or environmental sustainability can be mapped in a similar manner as characteristics and traits that distinguish types of diet and differences in levels of quality in a particular diet. Thus, using the method described herein, it is possible to quantify differences in diet quality based on health and to also quantify difference in diet quality based on environmental impacts of the measure of diet quality.

In one embodiment, a life cycle assessment may be performed of representative traits of a particular diet type. As discussed above a life cycle assessment (LCA) can demonstrate how the food, and/or the refining of such food affects the environment, from planting and harvesting of the food, transportation, and refining of the food and until the food becomes waste or is recycled or composted.

Life cycle assessment can be evaluated by determining one or more of the following:

1) Acidification;
2) Eutrophication;
3) Global warming potential;
4) Photochemical smog; and
5) Land use Thus, in one embodiment, the present invention begins with diet types N that have each been mapped in terms of kind and objective quality measures to distinguish X levels of diet quality within each diet type N.

These levels of diet quality X of diet types N are translated into representative multi-day meal plans that highlight unique distinguishing characteristics of the level of diet X of the diet type N. This information is then converted into an inventory of foods that are translated into food images and these food images are transformed into composite images that represent food intake over a multi-day period for each level of diet quality X of each diet type N.

As described in provisional patent application No. 62/508,613, the subject matter of which is herein incorporated by reference in its entirety, the inventors of the present invention have developed a method of quantifying and mapping diet quality, the method comprising the steps of:

a) identifying a dietary pattern with a meaningful prevalence in a geographical region of interest;

b) cataloging defining and exclusive attributes of the dietary pattern;

c) prioritizing diet quality measures validated against health outcomes;

d) establishing features of a selected diet and the relative variance within the features;

e) identifying a sequence of dietary variants representing the relative variable within the features; and f) determining an appropriate degree of discrimination required to represent realistic variation in the dietary pattern.

The first step is to select a diet type N for analysis, which may be any one of a number of diet types that represent common diet types of a typical user in a geographical area of interest. In this instance, the procedure involves the step of identifying a dietary pattern with a minimal, meaningful prevalence (i.e., greater than or equal to about 5%) in the geographic region of interest. This step is repeated until about 95% of the general population of interest is represented. The dietary pattern may be one such as, for example, vegan, Southwestern, etc. Prevalence is preferably based on published literature/epidemiological analysis when possible and, if necessary, with expeli opinion/personal experience as a contingency, The resulting product is a general diet type N that can be used to populate a ROW in the DQPN map.

The next step is to establish an exclusive, operational definition of the diet type N. In this instance, the procedure involves cataloguing the defining and exclusive attributes of the diet type in question. The definition and exclusive attributes of the diet in question may be one such as, for example, a vegan diet consists of a plant food diet exclusive of all meat, fish, eggs, dairy and seafood. The resulting product is a specific and exclusive diet type N, suitable for mapping in a DQPN ROW.

The next step is to identify a suitable measure of objective diet quality applicable to the diet type N. In this instance, the procedure involved prioritizing diet quality measures to optimize health and/or to minimize adverse environmental impacts to establish appropriate stratification based on objective quality, for example, correspondence with health outcomes, rather than fidelity to the diet principles, per se. The resulting product is an applicable diet quality measure for a given ROW of the map, wherein each cell in the row of this map represents a level of diet quality X of the diet type N.

The next step in the process is to address 'adherence to type' as warranted. In this instance, the procedure involves establishing the salient features of a given diet type N and the relevant variance in them that account for adherence to that diet type N with greater or lesser fidelity. This step can be qualitative and subjective, based on a validated metric, or rely on Principal Component Analysis (PCA) or a related method. The differentiation among diet TYPES and the fidelity to given TYPE across the tiers of objectively measured quality are informed by Principal Component Analysis. Similarly, the mapping of PDDCs is informed by this same method for delineating the salient and differentiating attributes of a given diet type, and in particular, those most reliably associated with given health effects.

For certain diet types, such as 'low carb', there may be poor correlation between adherence to the principles of the diet and objective measures of diet quality. In such cases, the two will be addressed sequentially; first by establishing tiers of 'fidelity' to the diet principles. To do this, the defining attributes of the diet that account for its application with varying degrees of fidelity should be catalogued. So, for instance: high-fidelity to a low-carb diet would exclude more carbohydrate sources (grains, legumes, etc.) than a low-fidelity version of the same diet. IF AND AS WARRANTED, Principal Component Analysis may be considered to establish a graded sequence of 'fidelity to type' tiers. The resulting product is a principal of determinants of fidelity to diet type, and optionally, but preferably, a graded sequence of diet prototypes representing variable levels of fidelity and/or adherence.

The next step in the process is to stratify by score or by 'principal determinants' of score. In this instance, the procedure involved a sequence of dietary variants representing fidelity/adherence that are compared to the principal determinants of diet quality in a preferred, objective metric, such as, the AHEI, to determine if 'fidelity' and 'quality' are, for this given diet, positively correlated, inversely correlated, or other. To illustrate: the 'operational' definition of a Paleo diet might emphasize minimally processed meats, vegetables, fruits, nuts, and seeds without grains, legumes or dairy. Objective measures of diet quality might pertain poorly to assessments of the Paleo diet, but they translate into higher scores with a rising intake of vegetables, fruits, nuts and seeds; generally higher scores with fish intake than with meat intake; and generally higher scores with unprocessed as compared to processed meat intake.

Accordingly, by way of example, the Paleo diet could be stratified IN ACCORD WITH these principal determinants of objective diet quality measures as follows:
1. The lowest quality tier has the most meat, and the most processed meat, relative to fish, vegetables, fruits, nuts, and seeds;
2. The next higher tier has an emphasis on meat, but not processed meat;
3. The next higher tier has an emphasis on meat and fish;
4. The next higher tier has an emphasis on game and fish;
5. The next higher tier has an emphasis on fish;
6. The highest tier has the greatest emphasis on a variety of vegetables and fruits, making up the bulk of calories, with a lesser portion of the diet from fish and game.

Thus, in the case of the Paleo diet, the determination might be made that 'fidelity' and 'quality' are NEITHER directly nor inversely correlated, since a high-fidelity, plant-predominant Paleo diet would generate a higher quality score than a comparably high-fidelity, but more meat-predominant version of the same diet. The key elements of diet stratification thus involve one of two methods: either stratify directly on the basis of objective quality scores OR translate the objective quality scores into principal determinants and stratify based on the 'subjective' alignment of variants of a given diet with those principal determinants, and then formally score that sequence of diets to corroborate directional correctness. The resulting product is a stratified sequence of variants of the diet in question, arranged from lower quality to the left, higher quality to the right. The final product may or may not be arranged in graded order of 'fidelity.'

The next step in the process is to estimate "ideal" stratification. In this instance, the procedure is to determine the appropriate degree of discrimination, such as, the number of quality tiers, needed to represent realistic variation in the practice of the diet type to represent levels of diet quality X. This can be obtained experience and professional judgment, as well as review of representative dietary intake assessment instructions from suitable populations. The goal is to have enough tiers of quality (levels of diet quality X) to develop images that closely approximate the diet of any given, real-world consumer and to avoid the need for excessive tiers that add clutter without clarity. The resulting product in a graded sequence of dietary variants, with an ideal number of tiers specified.

The next step in the process involves establishing numerical "scores" for relevant tiers. In this instance, the procedure involves a number of tiers which are selected for a given diet that will determine the score ranges from the preferred metric, such as AHEI, to produce the maximal separation of dietary variants across the range from lowest to highest quality. The tiers should be situated symmetrically, for example, if there are 15 tiers, they should be spaced evenly across the expanse of 5 quintiles. The resulting product is to target scores, within narrow, specific tolerances, based on a preferred quality metric, that are used to fix the location of a given variant of a given diet in the map. Diets of a lower quality are always to the LEFT of diets of higher quality. Quality rises in all rows from left to right.

The next step in the process is to create a menu corresponding to a cell. In this instance, the procedure involves a given cell in the DQPN map which represents a specified diet type at a target quality level, characterized by principal determinants. There are two ways to generate a menu or meal-plan based on this information: (a) assemble a prototype of foods/dishes/meals designed to hit the target score and emphasizing the principal determinants; or (b) identify several ACTUAL dietary intake assessments that correspond to the diet type and target score and hybridize those into a representative prototype. The diet prototype may be assembled and then scored, and then modified as required to move the resulting score closer to the stipulated target. Menus are preferably put together to correspond both with quality scores and with 'real world' eating patterns based on experience.

The intent is to establish prototypes of actual, prevailing dietary patterns. The detailed method of the menu design also includes the use of the HEI Component Score Template and/or the AHEI Component Score Template or other similar validated measure of diet quality, which involves entering the ideal component scores for each quality tier per dietary pattern. The ideal HEI-Score and/or AHEI Score range (or other similar validated measure of diet quality) can then be assigned per quality tier per dietary pattern, followed by assigning the percent goal range for macronutrients, for example, Carbs, Fat, Protein, and for any other relevant nutrients, and then assigning the food group/component amounts per quality tier and specific food examples per food group/components. In one embodiment, the goal is to aim for approximately 2500 kcal per day for up to 7 days, for each quality tier per diet type. The menu analysis may comprise entering food data into an established and validated nutrient analysis software program for nutrient analysis, and then adjusting specific food examples, if necessary. One such software program is the Nutrition Data System for Research (NDSR) dietary analysis program, available from the Nutrition Coordinating Center, University of Minnesota.

The final step in menu analysis is to export output data files. HEI-Scoring and/or AHEI-Scoring would consist of applying the output data files (for example, into the HEI Calculation Workbook), then obtaining and reviewing the HEI-Scores and/or AHEI-Scores and adjusting menus, if necessary prior to entering the HEI-Scores and/or in AHEI-Scores in working documents, such as the Preliminary DQPN Photo Map. The resulting product is a menu or meal plan populating a given cell in the map.

The goal is to establish, for each diet, the dietary critical mass (DCM), which is the minimal quantity of food, measured in units of 'typical daily intake,' necessary and sufficient to represent the breadth and variety of a given diet in a composite image so that it is readily recognizable, but free of excess that does not contribute to recognition. For diets that natively include more variety, the DCM will be higher, and for diets that have little variety and routinely repeat the same, small number of foods, the DCM will be lower. Regardless of the variable DCM for each type of diet, ALL DIETS are standardized to the same number of days so that variations in quantity of food per image do not introduce unintended distractors. For diets with DCMs, rather than the extra work of inventorying additional days, the minimally adequate number of days can be inventoried, and then multiplied to produce the STANDARDIZED-DCM. For each diet, the DCM is analyzed for nutrient levels, including calories. In one embodiment, the DCM is analyzed for 150 different nutrient levels.

The next step in the process is to amplify the menu to a period of time, which may be one day, several days or a full week. In this instance, the procedure involves the DQPN map showing that each image is intended to represent a typical time period of dietary intake. This may be achieved by developing seven distinct days that share the type, principal determinants, and quality score, or by developing a multi-day menu plan from the start. The time period may be represented as a mix of ingredients, dishes, and meals and NEED NOT be represented as a specific number of specific meals and snacks. If menus are assembled day-by-day, they must be expanded to represent a prototypical week. They do NOT need to be structured as specific meals and snacks, but rather should represent the total array of foods consumed in a 'typical time period.' The resulting product is a representative, time period-long meal plan corresponding to diet type, quality score, and principal determinants. While Applicant has determined that a week is a preferred period of time, the period of time may be selected to be at least one day or at least two days or at least three days or another selected time period. The analytics and specifications for each of the plurality of composite images representing each level of diet quality X of each diet type N can then be calculated.

The next step in the process is to inventory foods in specific portions. In this instance, the procedure is to specify the ingredients, dishes, and meals included in the menu plan, and establish the relative proportions of each variety of food so the quantitative representation is accurate. To prepare for photography, an exact inventory of foods and their relative quantities are necessary. The resulting product is a quantitative menu plan inventory.

The next step in the process is to specify relevant preparation details. In this instance, the procedure involves a given menu plan which may include pre-packaged food items, and meals prepared at home. The next part of this step is to establish the differential representation of these, either by showing ingredients versus packaged food, and/or by showing home-prepared meals on dishware. The composite images may differentiate between meals prepared at home and pre-prepared food consumed outside the home or at home; and such details need to be specified for each cell for appropriate representation. The resulting product is a menu plan inventory with appended description of food preparation representation.

The final step in the process is to finalize the cell description for photography and creation of the composite image. In this instance, the procedure involves establishing the final, detailed, fully characterized food inventory for styling and photography. Once the final, detailed fully characterized inventory of foods, ingredients, ingredients, dishes and meals representative of a particular diet quality level X of a particular diet type N for a period of time is styled, it is photographs to create a composite image representative of the particular diet quality level X of the particular diet type N and this step can be repeated for each diet quality level of each diet type N. The final, detailed description should translate into both a shopping list, and instructions for food prep necessary before photographing. The resulting product is a shopping list and food prep instructions.

As set forth herein, each ROW in a DQPN map will depict rising diet quality from left to right.

Each COLUMN in a DQPN map will represent movement across diet types. Animal-food predominant diets, such as, Paleo; low carb. Will be at the bottom; omnivorous diets, such as, Mediterranean; Flexitarian, will be in the middle; and plant predominant diets, such as, vegetarian; vegan, will be at the top. Thus, there is a gradient from animal-food predominant to plant-food predominant from bottom to top.

The use of Principal Component Analysis, and the establishment of the principal determinants of the exclusive contents for a given cell in the map can be used as the PDDCs (principal differentiating dietary components) that characterize the 'steps' between a given cell and its neighbors.

Endo-PDDCs refer to the principal differentiating features among the quality tiers of a given diet across a row.

Exo-PDDCs refer to the principal differentiating features across diet types; the general direction at any given quality level is across an expanse from animal-food predominant (bottom of map) to plant-food predominant (top of map).

Omni-PDDCs refer to the principal differentiating features that establish directionality for the entire map, for example, highly processed and animal-food predominant at the bottom left; minimally processed and plant-food predominant at the upper right.

Once the plurality of dietary patterns has been identified, a dietary score may be assigned to each of the plurality of dietary patterns taking into account variations in region, culture, diet character and nutritional quality. This dietary score takes into account both the dietary quality and the environmental impacts of the particular type of diet and level of diet quality within the diet. In one embodiment, this dietary score is an integer between 1 and 10. Thus, the lowest level of diet quality within an identified diet would be given a score of Q1 and the highest level of quality within an identified diet would be given a score of Q10. However, it is noted that this dietary score may be determined on another scale such as Q1 to QS, or Q1 to Q6, or Q1 to Q7, etc.

Furthermore, once these pluralities of dietary patterns are identified, a life cycle assessment can be performed of specific exemplary foods for each diet/level of diet quality to provide an environmental score, which in one embodiment may a score between 1 and 10. Thus, the level of diet quality having the most negative environmental impacts would be given a score of E1 and the level of diet quality having the least environmental impacts would be given a score of E10. It is also noted that the environmental score may not directly correlate with the dietary score. For example, even the highest quality Paleo diet, which is given a score of Q10 for Paleo diets may have more negative environmental impacts and thus be assigned a score of E6 or E7 for environmental sustainability, while the highest quality vegan diet may be given a score of Q10 for diet quality and E10 for environmental sustainability.

In order to determine the environmental score of each type of diet and level of diet quality within the type of diet, a life cycle assessment can be performed of exemplary foods within the diet. Thus, a life cycle analysis may be performed on one or more of the following:
1) meats, including red meat, pork, chicken, etc.;
2) fish, including shellfish;
3) eggs;
4) dairy, including milk, yogurt, cheese;
5) grains, including rice, wheat, etc.
6) exemplary fruits and/or vegetables, focusing on different types and growing methods;
7) packaged/processed foods, e.g., frozen dinners, crackers, cookies, etc.
8) soft drinks; and
9) other exemplary foods.

Given that diets can be mapped using common coordinates, using the process described above, it is possible to arrange diets relative to one another using these common coordinates to create desired gradients directed to minimizing environmental impacts and/or modifying diet patterns to reduce environmental impacts. For example, diets may be arranged relative to one another to create a gradient most to least likely to include meat, in combination with other objective benchmarks of diet quality.

Using an objective measure of overall environmental impact, the diets—represented in such a map can be organized to create a continuous gradient in environmental impact from most to least. In one embodiment, the measure of overall environmental may be life cycle analysis as described above, or another related measure as would be known to those skilled in the art. The continuous gradient in environmental impact may include, for example, global warming potential water utilization, land use, eutrophication, acidification, photochemical smog, etc.

In general, diets of higher objective nutritional quality/better for health are expected to correlate with diets of lesser environmental impacts. However, diets of equivalent nutritional quality for health may vary with respect to environmental impacts and vice versa. In other words, in diets of equivalent nutritional quality, a diet that is of maximum health may not be the best diet with respect to environmental impacts, especially if the diet is based on foods that are complementary foods that have a different environmental impact as determined using LCA (for example, greenhouse-grown versus field-grown tomatoes).

Using diet quality photo navigation methodology as described in Applicant's co-pending applications, any diet quality level X of any diet type N can be represented in a composite image as fully analyzed prototypes. In this instance, the Diet Ideal becomes the ideal diet for reducing adverse environmental impacts.

In addition, the route customizing algorithm in this case becomes a coaching app to guide the user incrementally from the baseline Diet ID to a goal Diet Ideal that is chosen to minimize adverse environmental impacts.

As with the application No. 62/508,613, the guidance based on the library of composite images can be further refined with specific filters. In the case of adverse environmental impacts, these filters may include, for example, organically versus conventionally grown foods, locally sourced versus transported, in season versus out-of-season, GMO versus non-GMO, by way of example and not limitation.

In one embodiment, and as discussed above, the method further comprises the step of selecting a number of tiers to determine a score range to produce a maximal separation of dietary variants across a range from most adverse environmental impacts to less or least adverse environmental impacts. This may overlap or coincide with dietary variants of "lowest" or "highest" dietary quality, but the intent is different. In addition, these tiers of environmental impacts can be arranged from most adverse environmental impacts lowest to highest quality, wherein the tiers are arranged symmetrically across an expanse of quintiles, wherein each tier comprises a plurality of cells as shown in FIG. 1.

In addition, as described herein, each cell in the plurality of cells represents a specific diet quality level of X of a specific diet type N. The method may further include the step of generating a meal-plan corresponding to quality scores and to eating patterns based on experience. Each cell in the plurality of cells preferably depicts an image of a typical week of dietary intake for an individual or family. In one preferred embodiment, the image depicts a typical week of dietary intake. In other preferred embodiments, the image may depict a different period of time, such as one day, two days, several days, two weeks, several weeks or even one month.

The method may also include the step of establishing a meal plan based on the dietary intake, including the step of specifying food ingredients and dishes to include in the meal plan, wherein the relative proportion of each variety of food is established to produce an accurate quantitative representation.

While the DQPN route algorithm will append adjacent diet types to extend the quality scale, these may all be presented as selected diet types in a user interface that incorporates the methods described herein. So, for instance, if a user chooses a "flexitarian" diet and wants the highest possible quality and the highest quality version of that diet type migrates over to the Mediterranean diet row, then the top-quality Mediterranean diet is cross-referenced as the highest-quality flexitarian diet so that it also shows up as an option in that category.

It is further noted that the widest range of applicable diet quality levels X is not necessarily the full range. For example, the lowest quality version of a vegetarian diet would be made up of highly processed foods but would exclude meat and may also have the most adverse environmental impacts. The lowest quality version of a mixed/omnivorous diet would almost certainly score even lower, because it too would be made up of highly processed foods. But even though the "next lowest scoring diet" on the continuum might be an omnivorous selection, it would NOT make sense to present this as a choice to someone who has indicated that they are, or wish to be, vegetarian. Thus, it is important that the range of selections should be extended as far to both sides as they can be while adhering to the basic diet type (baseline or goal) indicated by the user.

The present invention also relates to a web-based or mobile application that can be used by consumer to evaluate the overall quality of their current diet and/or the environmental impacts of their current diet and provide affirmative steps to coach them to a higher quality diet and/or a more environmentally sustainable diet. An application program interface (API) can be used to program a computer program product that includes a graphical user interface (GUI) and that can be integrated into and delivered via an on-line platform or program, and that is viewable and executable on a computer, tablet, smart phone, or other similar device.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. A non-limiting list of computer-readable medium include the following:
an electrical connection having one or more wires,
a portable computer diskette;
a hard disk,
a random-access memory (RAM),
a read-only memory (ROM),
an erasable programmable read-only memory (EPROM or Flash memory),
an optical fiber,
a portable compact disc read-only memory (CDROM),
an optical storage device, and/or transmission media such as those supporting the Internet or an intranet, or a magnetic storage device.

The computer-usable or computer-readable medium can even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

As described herein, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object-oriented programming language such as JAVA, SMALLTALK, C++ or the like and conventional procedural programming languages, such as "C" or similar programming languages. The program code may execute entirely on the user's computer, partly on the user's computer, as a stand-alone software package, partly on the user's computer and partly on a remote computer or entirely on the remote computer or server. The remote computer may be connected to the user's computer through any type of network, including, for example, a local area network (LAN) or a wide area network (WAN), or the connection may be made to an external computer (for example, through the Internet using an Internet Service Provider).

In one embodiment and as illustrated in FIG. 2, the system comprises an environment for managing the processes in accordance with the invention. The environment comprises a computer infrastructure 10 that can perform the processes described herein using a computing device 20. The computing device 20 includes a Diet Identification Tool 25, a Composite Image Tool 35, An Environmental Sustainability Tool 45, a Diet Optimization Tool 55, a Calculation Tool 65, a Coaching Tool 75, a Diet Tracking Tool 95 and a Navigation Tool 105. These tools are configured to and are operable to provide a consumer with a dietary score of their current diet, a dietary score of their "Ideal" diet, and coaching/inspirational tips to move from their current diet to their ideal diet based on determined information. Thus, the processes described herein are under the control of and are controlled by program control 50.

Thus similarly to a global positioning device or App for navigating a user from point A to point B, the present invention provides the tools for a user to:
1) identify where they are (baseline diet);
2) identify where they would like to go (goal or "ideal" diet);
3) track changes over time; and
4) navigate to their destination through a series of steps.

The computing device 20 includes a processor 30, a memory 40, an input/output (I/O) interface 60, and a bus 62. The memory 40 can include local memory employed during actual execution of program code, bulk storage, and cache memories which provide temporary storage of at least some program code in order to reduce the number of times code must be retrieved from bulk storage during execution.

The computing device 20 is in communication with an external I/O device/resource 80. The I/O device 80 can interact with the computing device 20 or any device that enables the computing device 20 to communicate with one or more other computing devices using any type of communications link. The external I/O device/resource 80 may be keyboards, displays, pointing devices, etc. Additionally, in some embodiments, the computing device 20 includes a storage system 90.

The processor 30 executes computer program code (e.g., program control 50) processes on computer media, which is stored in memory 40 and/or storage system 90. While executing computer program code, the processor 30 can read and/or write data to/from memory 40, storage system 90, and/or I/O interface 60. The bus 62 provides a communications link between each of the components in the computing device 20.

The computing device 20 may comprise any general-purpose computing article of manufacture capable of executing computer program code installed thereon (such as, for example, a personal computer, server, handheld device, etc.). However, it is understood that the computing device 20 is only representative of various possible equivalent computing devices that may perform the processes described herein. To this extent, in embodiments, the functionality provided by the computing device 20 can be implemented by a computing article of manufacture that includes any combination of general and/or specific purpose hardware and/or computer program code. In each embodiment, the program code and hardware can be created using standard programming and engineering techniques, respectively.

Similarly, the computer infrastructure 10 is only illustrative of various types of computer infrastructures for implementing the invention. For example, in embodiments, the computer infrastructure 10 may comprise two or more computing devices (e.g., a server cluster) that communicate over any type of communications link, such as a network, a shared memory, or the like, to perform the processes described herein. Further, while performing the processes described herein, one or more computing devices in the computer infrastructure 10 can communicate with one or more other computing devices external to computer infrastructure 10 using any type of communications link, including any combination of wired and/or wireless links; any combination of one or more types of networks (e.g., the Internet, a wide area network, a local area network, a virtual private network, etc.); and/or utilize any combination of transmission techniques and protocols.

In one preferred embodiment, the present invention relates generally to a system implemented in hardware comprising:

a computer infrastructure operable to implement a diet identification tool configured to identify qualities of a diet of a user on a graphical user interface based on composite images selectable by the user; and a composite image tool, wherein the composite image tool is populated with a library of composite images, wherein each composite image depicts a unique inventory of proportions of foods, ingredients, dishes and meals representative of a particular diet quality level X of a particular diet type N for a period ohime, and wherein the library of composite images is accessed using the diet identification tool on the graphical user interface, and at least one of:
1) an environmental sustainability tool to identify an environmental quality of the diet of the user based on composite images selected by the user;
2) a diet optimization tool configured to allow the user to select a different diet type N and/or diet quality level X using the composite image tool and the diet identification tool;
3) a calculation tool configured to calculate personalized nutrient levels and personalized environmental impacts of the user based on inputted information of the user, wherein the graphical user interface is configured to allow the input of the information and to display the calculated personalized nutrient levels to the user;
4) a coaching tool populated with a plurality of coaching tips comprising discrete steps and changes to allow the user to move from one N diet type to a different N diet type and/or from one level of diet quality X to a different level of diet quality X, wherein the graphical user interface is configured to display the coaching tips to the user;
5) a diet tracking tool, wherein the diet tracking tool allows the user to change or update their diet type N, change or update their level of diet quality X, and compare changes in level of diet type N and level of diet quality X over time; and wherein the graphical user interface is configured to display the changes; and
6) a navigation tool populated with discrete steps to move the user stepwise from one level of diet quality X of one N diet type to a different N diet type and/or from one level of diet quality X to a different level of diet quality X, wherein the graphical user interface is configured to display a navigation route to the user.

In one embodiment, the system described herein comprises a computer infrastructure operable to implement the diet identification search tool, composite image tool, environmental sustainability tool, diet optimization tool, calculation tool, coaching tool, diet tracking tool, and navigation tool.

In another preferred embodiment, the present invention relates generally to a computer program product comprising a computer usable medium having readable program code embodied in the medium, the computer program product including at least one component that when executed by a processor is operable to:

A) display a menu of N diet types for selection by a user on a graphical user interface, B) display a first plurality of unique composite images of diet quality levels Xn, wherein each composite image contains images of foods in specific portions and depicts relative portions of ingredients, dishes and meals representative of the level of diet quality Xn of the N diet type selected by the user;

C) display a different plurality of unique composite images of diet quality levels Xn upon selection by the user of one of the unique composite images in the first plurality of unique composite images, wherein one composite image of the level of diet quality Xn is the same as in the display of the first plurality of unique composite images and at least one composite image is different;

D) display an input screen to allow the user to input personal information about the user on the graphical user interface, wherein the personal information may be one or more of gender, age, height, weight, and activity level;

E) display an input screen to allow the user to input diet modification information on the graphical user interface; and F) calculate a user specific assessment of diet quality and type for the user and display the calculated user specific assessment of diet quality and type to the user on the graphical user interface.

In addition, each unique composite image depicts relative portions of foods, ingredients, and dishes for breakfast, lunch, dinner and snacks over a multi-day period, where the foods ingredients, and dishes exemplify a level of diet quality X of an N diet type.

The diet modification information may comprise dietary preferences regarding specific ingredients, dishes, meals and/or foods and the input screen allows the user to input additions or subtractions in whole or in part of these specific ingredients, dishes, meals and/or foods. These dietary preferences may include one or more of alcohol, meat, poultry, fish, nuts, water, dairy, vegetables, fruits, refined grains, whole grains, legumes, fast food, sweets, and alcohol. This diet modification information may also comprise dietary restrictions such as dairy-free, gluten-free, shellfish-free, peanut-free, egg-free, nut-free, wheat-free, soy-free and alcohol-free and the input screen allows the user to input the dietary restrictions In one embodiment, it is further contemplated that the processes and system described herein may provide a business method that performs the steps of the invention on a subscription, advertising, and/or fee basis. That is, a service provider could offer to perform the processes described herein. In this case, the service provider can create, maintain, deploy, support, etc., a computer infrastructure that performs the process steps of the invention for one or more customers. In return, the service provider can receive payment from the customer(s) under a subscription and/or fee agreement and/or the service provider can receive payment from the sale of advertising content to one or more third parties.

As described herein, the computer program product may contain a coaching tool that is populated with a plurality of coaching tips comprising discrete steps and changes to allow the user to modify their diet from one N diet type to a different N diet type and/or from one level of diet quality X to a different level of diet quality X, and in which the graphical user interface displays the coaching tips to the user.

The computer program product may also contain a diet tracking tool. In this instance, the graphical user interface can display an input screen to allow the user to change or update their diet type N, change or update their level of diet quality X, and the graphical user interface is configured to display changes in level of diet type N and level of diet quality X over time.

The computer program product may also contain a navigation tool, wherein graphical user interface displays a navigation route or navigation steps to the user to move the user stepwise from one level from one N diet type to a different N diet type and/or from one level of diet quality X to a different level of diet quality X.

The present in invention also relates generally to a computer-based method for assessing diet type and quality of a user using the computer program product described herein, the method comprising the steps of:

A) selecting an N diet type from the menu of N diets displayed on the graphical user interface, wherein once the user selects the N diet type from the menu of N diets, the graphical user interface displays the first plurality of unique composite images of diet quality levels Xn, wherein each unique composite image of diet quality level X depicts a different level of diet quality Xn of the selected N diet type;

B) selecting a composite image of diet quality level Xn from the first plurality of unique composite images, wherein the display instructs the user to select the composite image of diet quality level Xn that approximates the user's current diet, wherein once the user selects the composite image of diet quality level Xn, the graphical user interface displays the different plurality of unique composite images of diet quality levels Xn, C) selecting a composite image of diet quality level Xn from the different plurality of unique composite images of diet quality levels Xn to more closely approximate the user's current diet;

D) optionally, iteratively repeating steps b) and c); In this instance, the step of selecting a composite image from the plurality of composite images may be repeated multiple times.

E) inputting personal information into the display screen of graphical user interface;

F) inputting diet modification information into the display screen of the graphical user interface, wherein the diet modification information comprises dietary restrictions or dietary preferences; and G) displaying on the graphical user interface a user specific assessment of diet type and diet quality based on the inputted information.

In the step of iteratively repeating steps b) and c); the selection of a composite image may be repeated multiple times. For example, if the user is first presented with images X1 and X2 and selects image X2, the user may then be present with images X2 and X3, If the user selects image X3, the user may then be presented with images X3 and X4. If the user again selects image X3, the selection process may stop, whereas if the user selects image X4, the iterative process may continue until the user is satisfied that they have selected the image that most closely resembles their diet quality level X of diet type N.

This method may further comprise the steps of:

A) displaying on the graphical user interface a different menu of N diet types, wherein the different menu of N diet types comprise optimal diets in terms of health and/or environmental sustainability;

B) selecting an N diet type from the different menu of N diet types displayed on the graphical user interface, wherein once the user selects the N diet type from the different menu of N diet types, the graphical user interface displays the first plurality of unique composite images of diet quality levels Xn, wherein each unique composite image of diet quality level X depicts a different level of diet quality Xn of the selected N diet type;

C) selecting a composite image of diet quality level Xn from the first plurality of unique composite images, wherein the display instructs the user to select the composite image of diet quality level Xn that approximates the user's goal diet, wherein once the user selects the composite image of diet quality level Xn, the graphical user interface displays the different plurality of unique composite images of diet quality levels Xn, D) selecting a composite image of diet quality level Xn from the different plurality of unique composite images of diet quality levels Xn to more closely approximate the user's goal diet;
E) optionally, iteratively repeating steps b) and c);
F) inputting diet modification information into the display screen of the graphical user interface, wherein the diet modification information comprises dietary restrictions or dietary preferences; and
G) displaying on the graphical user interface a user specific assessment of the goal diet type and diet quality based on the inputted information.

According to one aspect of the invention, a Diet Identification Tool 25 may identify a diet of a consumer based on composite images(s) selected by a user on the external I/O device 80. In one embodiment, the external I/O device 80 includes a graphical user interface (GUI). Thus, the consumer accesses computing device 20 through the I/O interface 80 and is presented with a series of composite images on the GUI. Upon selection of a composite image and using the system and method described herein, Program control 50 can then calculate/identify a dietary score for the user based on the composite images selected and display the dietary score to the user on the GUI.

According to one aspect of the invention, Composite Image Tool 35 is populated with a library of composite images, wherein the images comprise photographs that have been prepared by the methodology described above and comprising an inventory of foods in specific portions. The composite images each depict ingredients, dishes, and meals included in the particular menu plan, and establish the relative proportions of each variety of food so the quantitative representation is accurate. Composite images contained in the Composite Image Tool 35 can be displayed as images on the GUI of the external I/O device.

According to one aspect of the invention, the Environmental Sustainability Tool 45 identifies an environmental quality of a diet type N of a consumer based on the composite image selected by a user on the external I/O device 80. Then, the consumer accesses computing device 20 through the I/O device 80 and is presented with a series of composite images on the GUI. Program Control 50 can then calculate/identify an environmental score and display the environmental score to the user on the GUI.

According to one aspect of the invention, Diet Optimization Tool 55 permits a user to identify a different diet type N or level of diet quality X and presents composite images to the user of selection on the external I/O device 80. This different diet may be a different diet type N (i.e., flexitarian versus vegan), different in level of diet quality X and/or different in Environmental Score. The consumer accesses computing device 20 through the I/O interface 80 and is presented with a series of composite image on the GUI. Upon selection of an image, Program control 50 can calculate/identify a different dietary score or environmental score for the user based on the composite images selected and display the dietary score to the user on the GUI. The diet optimization tool may also comprise a diet personalization tool in which a user can identify one or more elements of diet to be added, reduced or removed from their diet, including alcohol/wine, meat, poultry, seafood, etc. In one example, the diet personalization tool can allow a user to modify the selected composite image with items that represent their preferences (e.g. swap white wine for red wine in the composite image).

According to one aspect of the invention, Calculation Tool 65 is configured to calculate personalized information about the user based on information inputted into the GUI of the I/O device 80. This input may include, for example, personalization information containing the level of diet depicted in the series of images, dietary restrictions, personal information of the user (i.e., gender, age, height, weight, etc.), activity level of the user, and other information. The program control 50 can then calculate personalized nutrient levels of the user based on the composite images selected and information inputted and then display this information to the user on the I/O device 80.

According to one aspect of the invention, Coaching Tool 75 is populated with coaching tips comprising discrete/incremental steps/changes that may be taken by a user to move from an initial level of diet quality X to a different level of diet quality X. Upon selection of a composite image of a desired or optimal diet type N of a user through the GUI of the I/O device 80, program control 50 can access the coaching tips contained in the Coaching Tool 75 and display these tips in a step-wise fashion to the user on the GUI so that the user can incrementally change their diet from a first/baseline diet N and level of diet quality X to a different diet type N and/or level of diet quality X. The coaching tool 75 may be configured to provide substitute or complementary items to the user.

For example, Coaching Tool 75 may be populated with coaching tips such as:
Type of diet: American (highly processed)>>>flexitarian>Mediterranean>>>vegetarian>>>vegan
Meat: Red meat—Grass-fed read meat>>>Red meat once/week>>>Red meat once/month>>>Red meat rarely
Poultry: Chicken/poultry—Free range>>>Organic>>>Substitute one or more meatless meals
Fish: Farm-raised>>>wild caught>>>particular types of fish
Produce: Eat more vegetables/fruits>>>refined/processed>>>canned>>>frozen>>>greenhouse grown>>>organic>>>field grown>>> in season
Shopping: Supermarket>>>farmer's market>>>community sponsored agriculture (CSA)>>>home garden
Packaging: Processed>>>canned>>>plastic-wrapped>>>cardboard>>>minimal>>>none
Origination of goods: International>>>regional>>>local>>>home garden
Level of refinement: heavily processed>>>canned>>>frozen>>>fresh>>>organic In an optional embodiment, the computing device may also comprise an item tool 85 that is configured to provide a grocery list for the consumer and information about the items on the grocery list for the consumer. The items may be listed on a manufacturer's or merchant's website or on other websites. Additional information such as "green" information, may be obtained about an item. For example, selecting the item may also give descriptive information, for example by a hyper-link to green information on the website or on the world wide web or Internet. The item tool 85 may also be employed to provide a profile which may be used to specify what characteristics of items are to be displayed.

In embodiments of the invention, a tool may perform one or more functions of another tool, or may employ one or more other tools to perform one or more functions.

FIGS. 3-36 depict screen shots of a GUI in accordance with one aspect of the present invention and provides an example of a methodology in accordance with the present invention.

FIG. 3 is an introductory screen in the GUI in which the user is invited to select their current diet type N from among a menu of diet types, FIG. 4 is another view of the introductory screen of FIG. 3 in which the user has chosen "American" as their current diet type N. FIG. 5 depicts a screen in the GVI in which the user can input information regarding any dietary restrictions. FIG. 6 is another view of the screen of FIG. 5 regarding dietary restrictions in which the user has indicated that they do not have any dietary restrictions.

Figure 7:
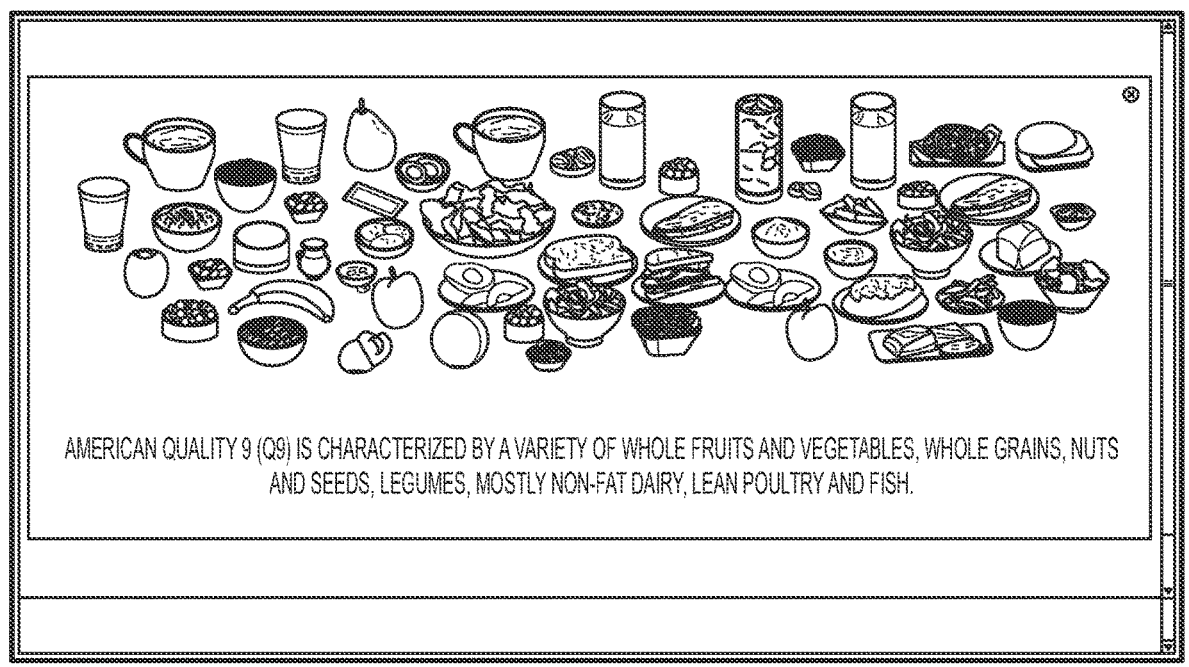

FIG. 7 is another screen in the GUI which invites a user to view a plurality of unique composite images, wherein each composite image represents a different level of diet X of the diet type N and to select the composite image that that looks most like their current diet. As seen in FIG. 7, these composite images each depict a unique inventory of proportions of foods, ingredients, dishes and meals representative of a particular diet quality level X of the particular diet type N for a period of time foods for breakfast, lunch, dinner and snacks over a multi-day period (i.e., several days or one week) and depict exemplary foods that are chosen to highlight the differences in the levels of diet shown. In addition, while FIG. 7 depicts a series of three unique composite images that are displayed to the user for section, the number of composite images displayed to the user may be two composite images, three composite images, or more (i.e., 4 or 5, etc.). However, the display of two or three images is preferred.

Figure 8:
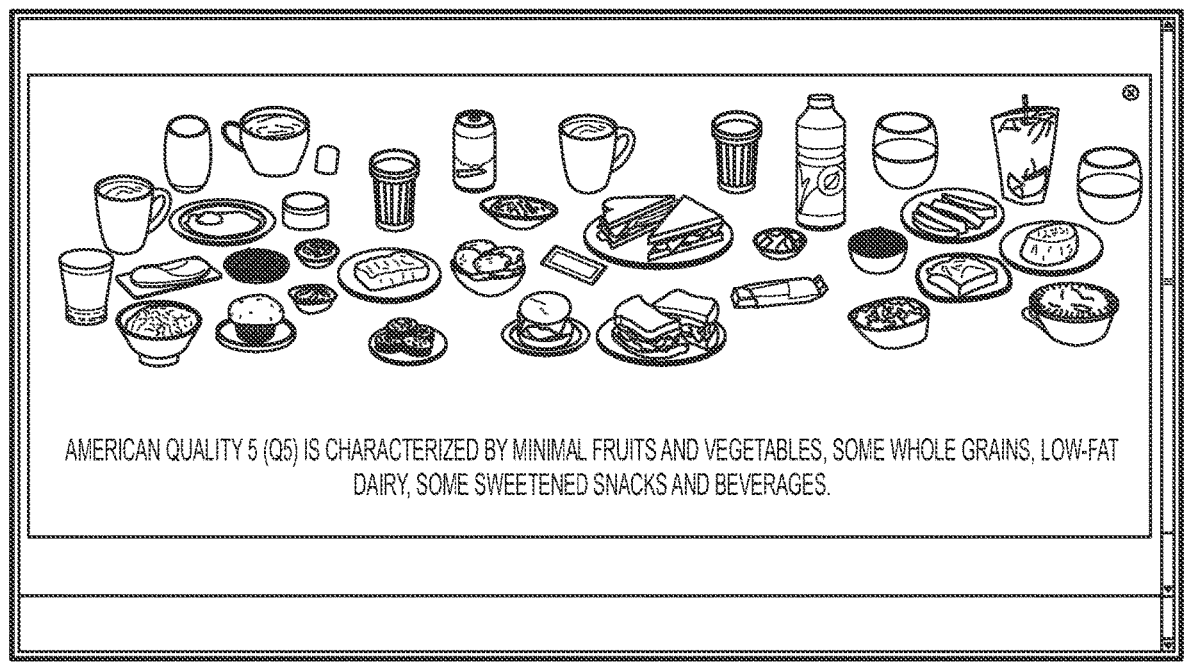
Figure 9:
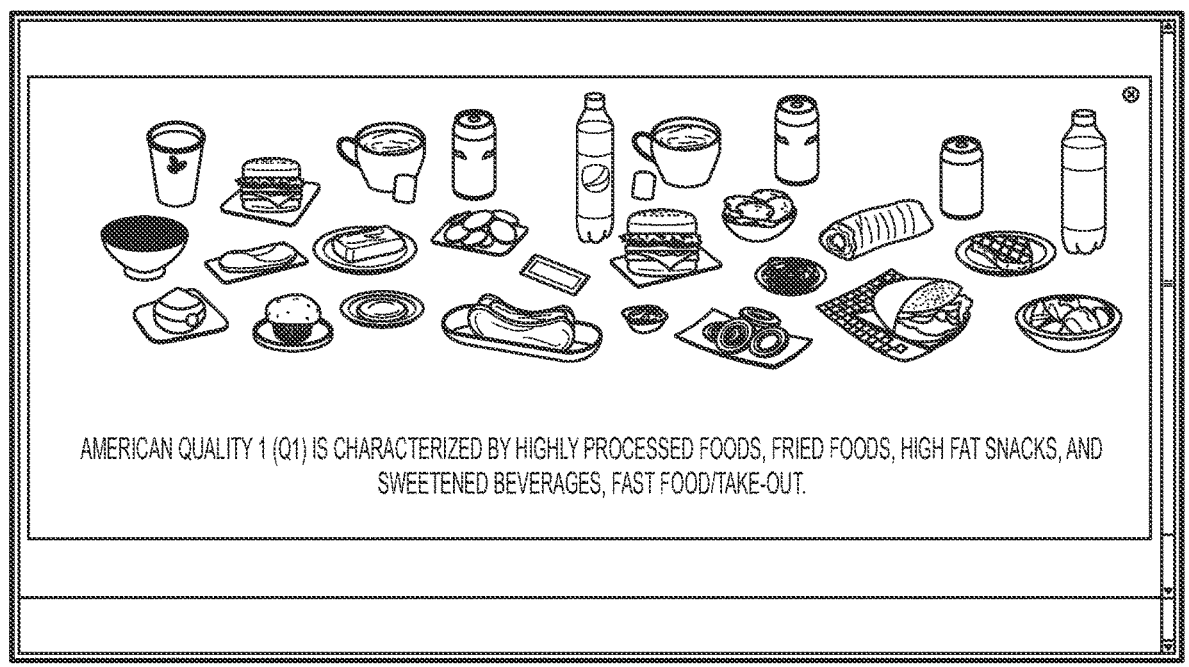
Figure 10:
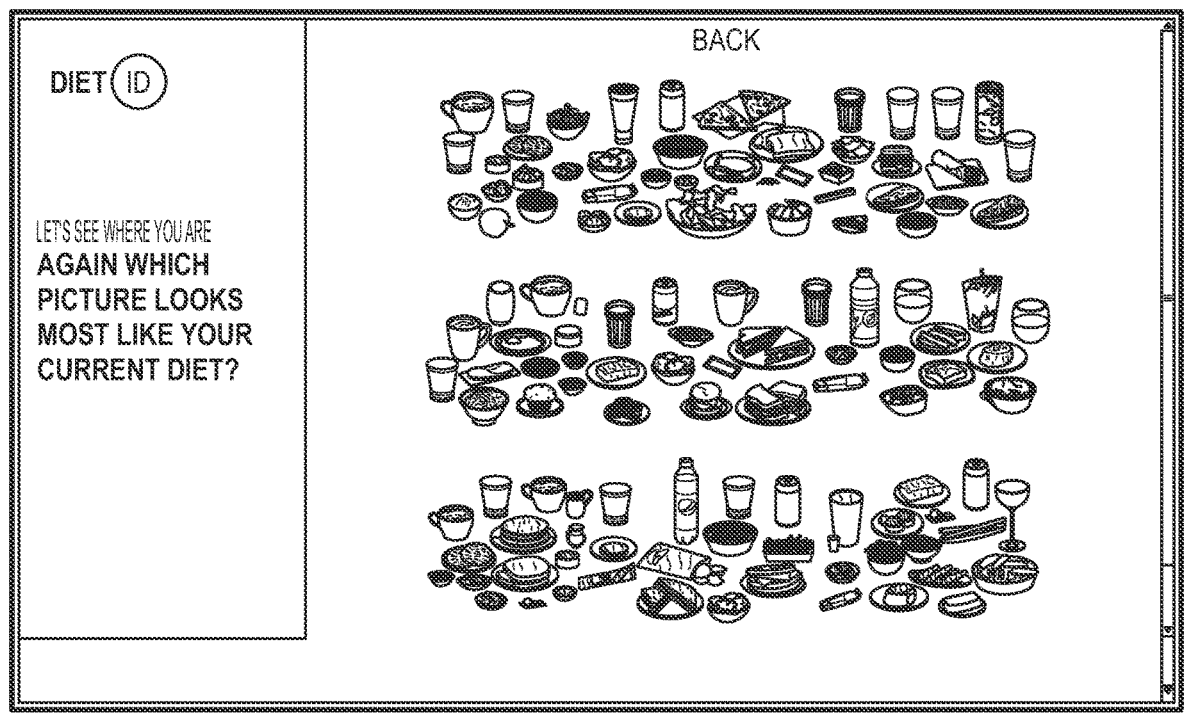
Figure 11:
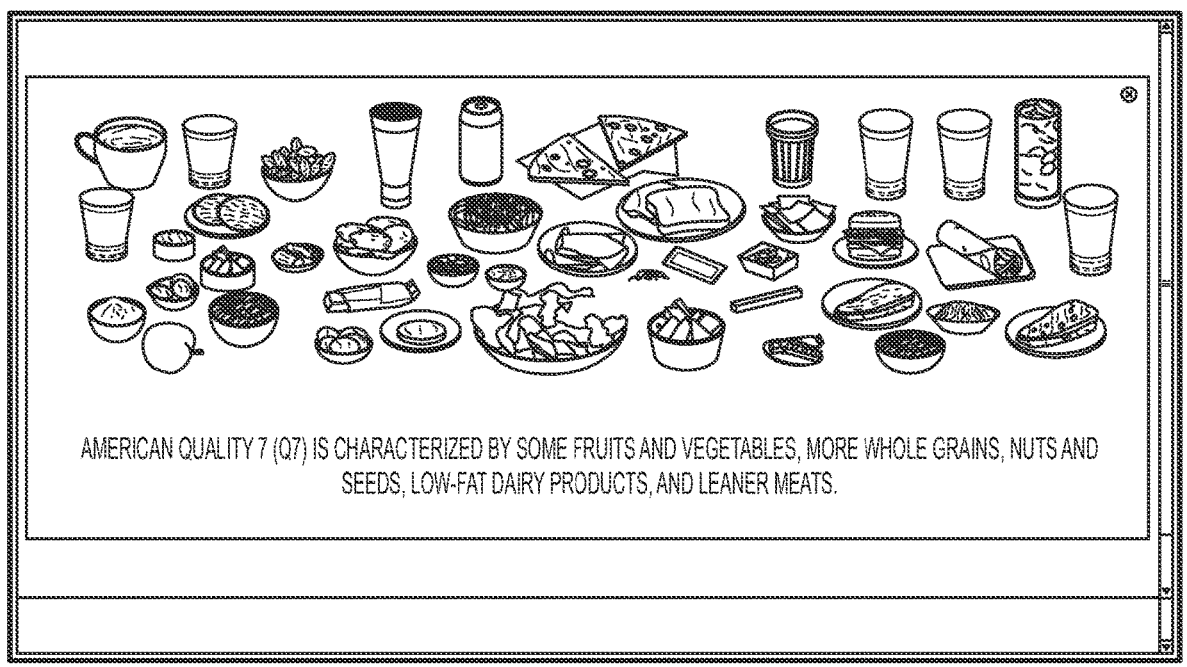

As shown in FIGS. 8-10, each composite image can be individually selected to obtain additional information on the particular level of diet X. Once a user selects a composite image that is representative of their current level of diet X, they are invited to view a second set of unique composite images as shown in FIG. 11 to refine their diet choices. As shown in FIG. 10, one composite image of the level of diet quality Xn is the same as in the display of the first plurality of unique composite images and at least one composite image is different.

Figure 12:
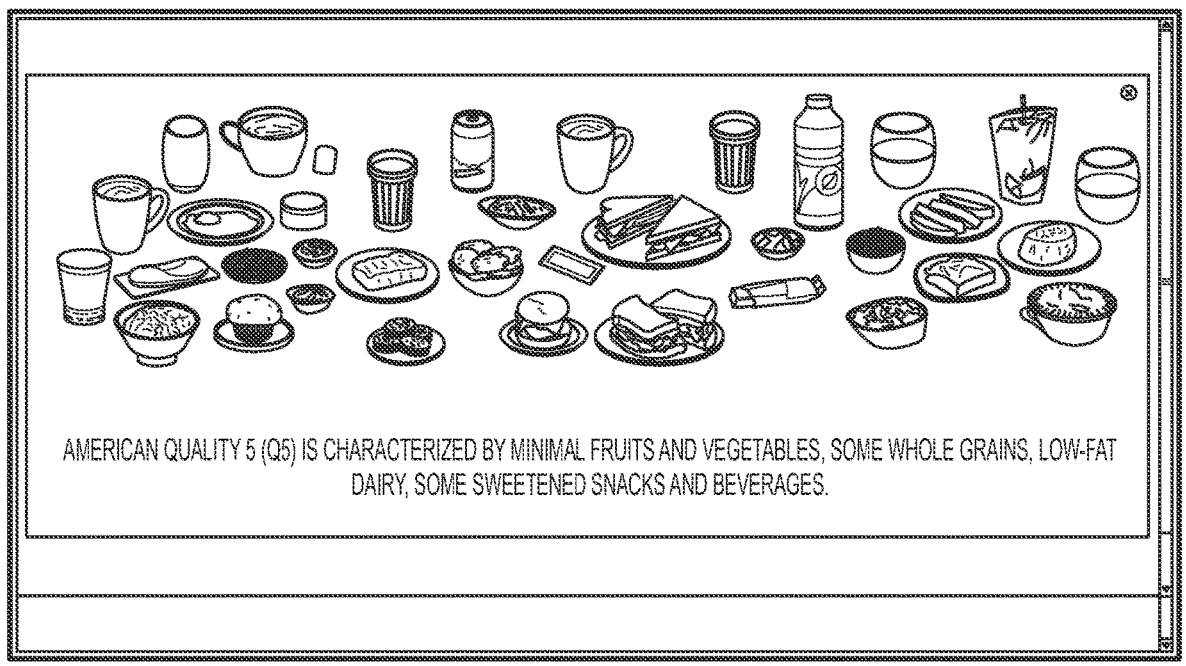
Figure 13:
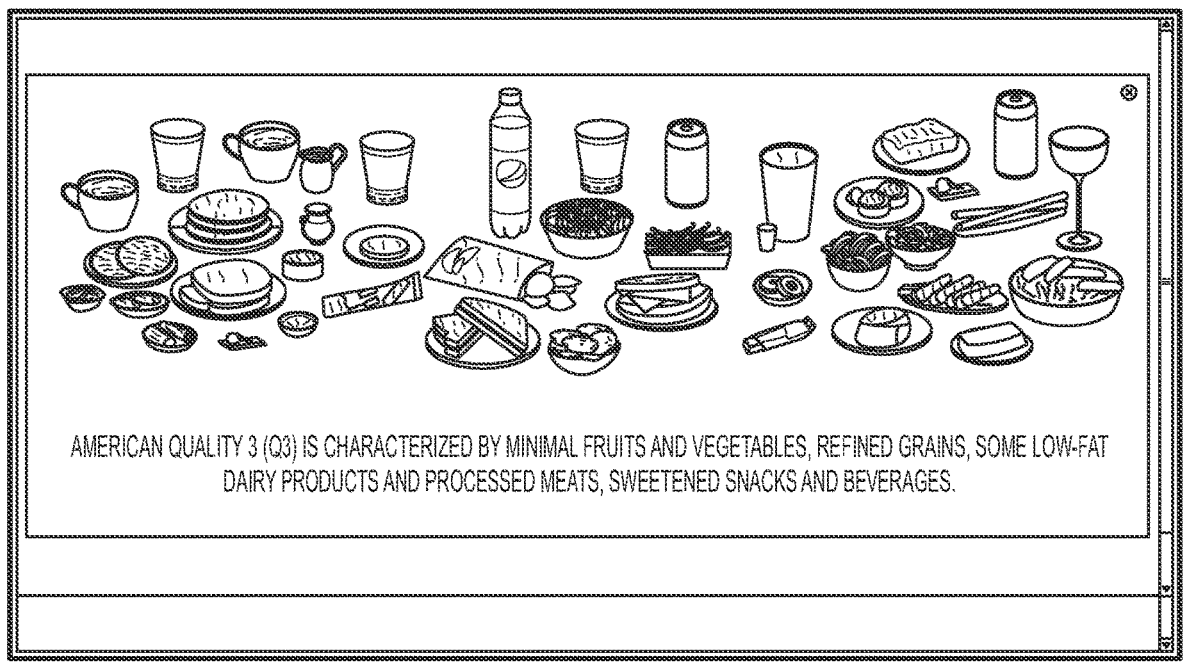
Figure 14:
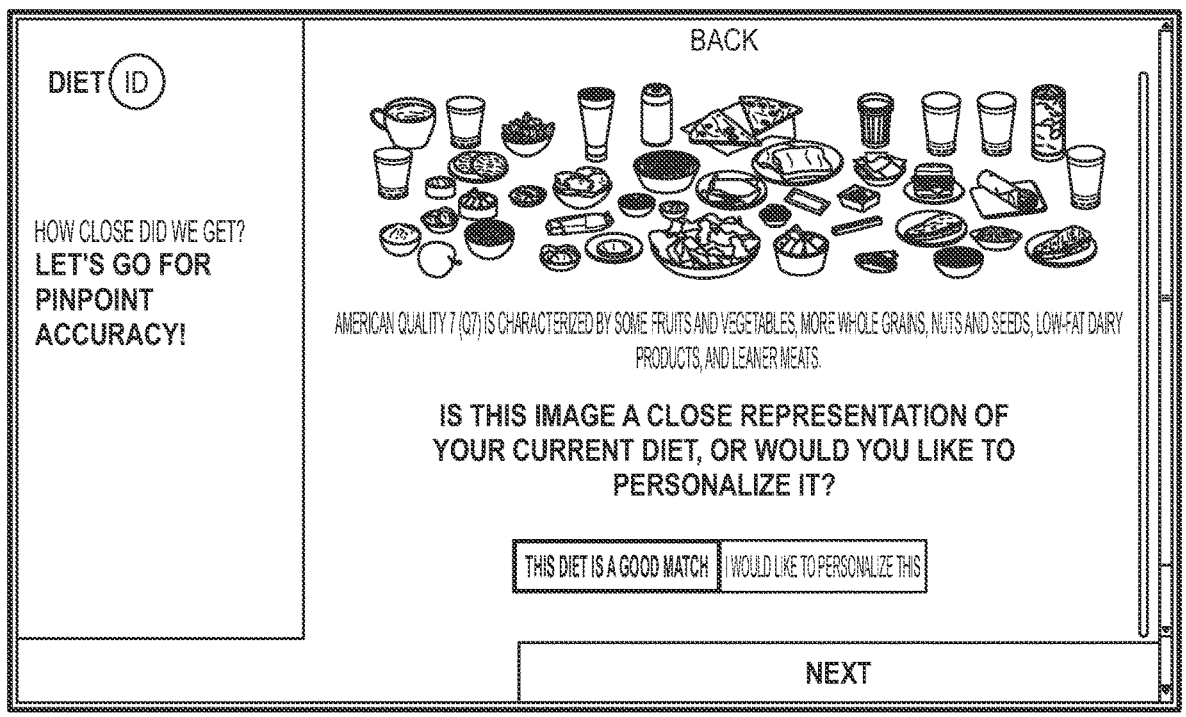

Again, and as shown in FIGS. 12-14, each composite image can be individually selected to obtain additional information regarding the particular level of diet. Thus, while in the first set of composite images, the composite images represent diet quality levels Q9, Q5 and Q1, or the high, low and average diet quality levels of a typical "American" diet, the second set of composite images represents diet levels Q7, Q5, and Q3 so that the user can more closely align a composite image to their current diet.

Figure 15:
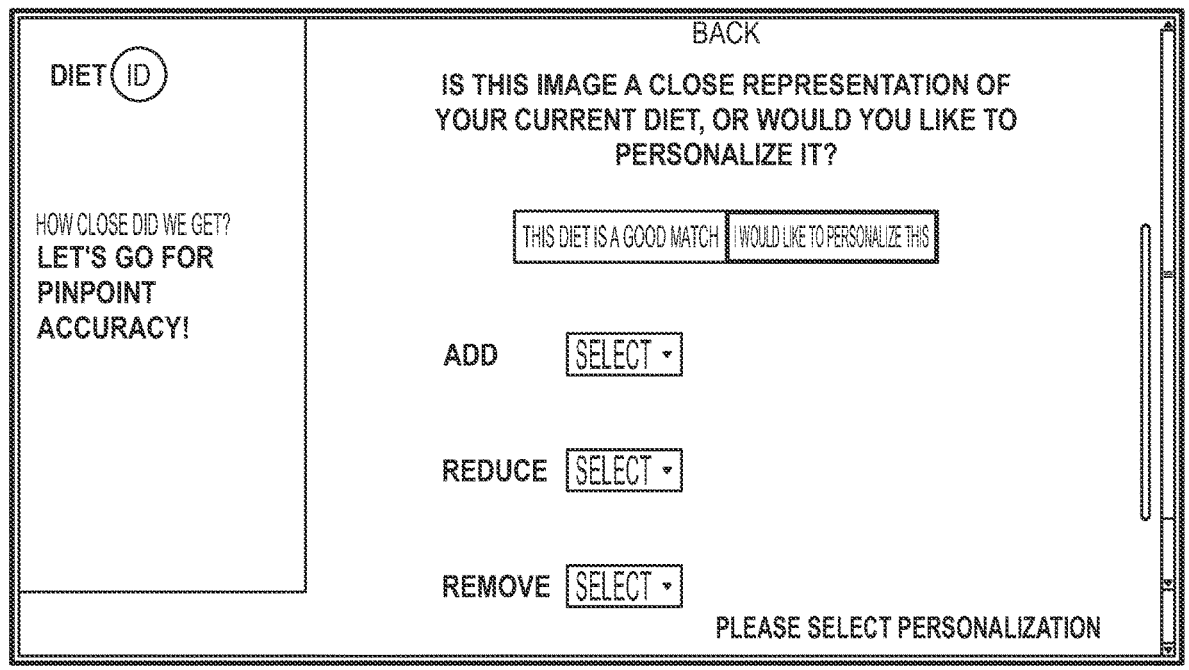
Figure 16:
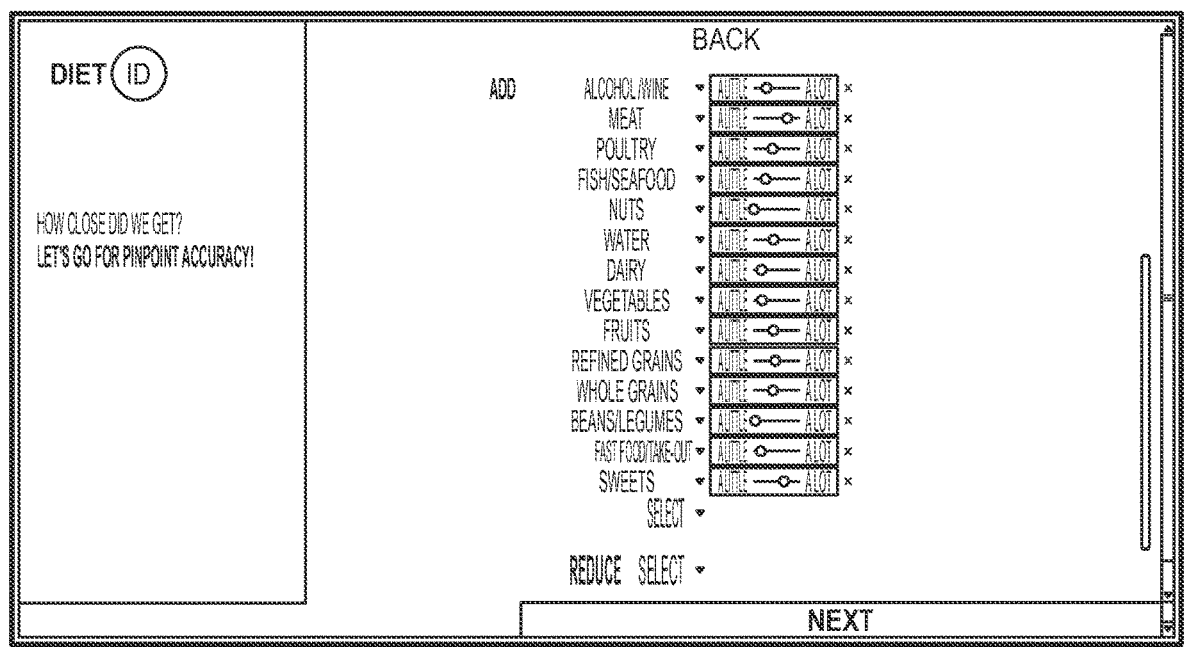
Figures 17, 18:
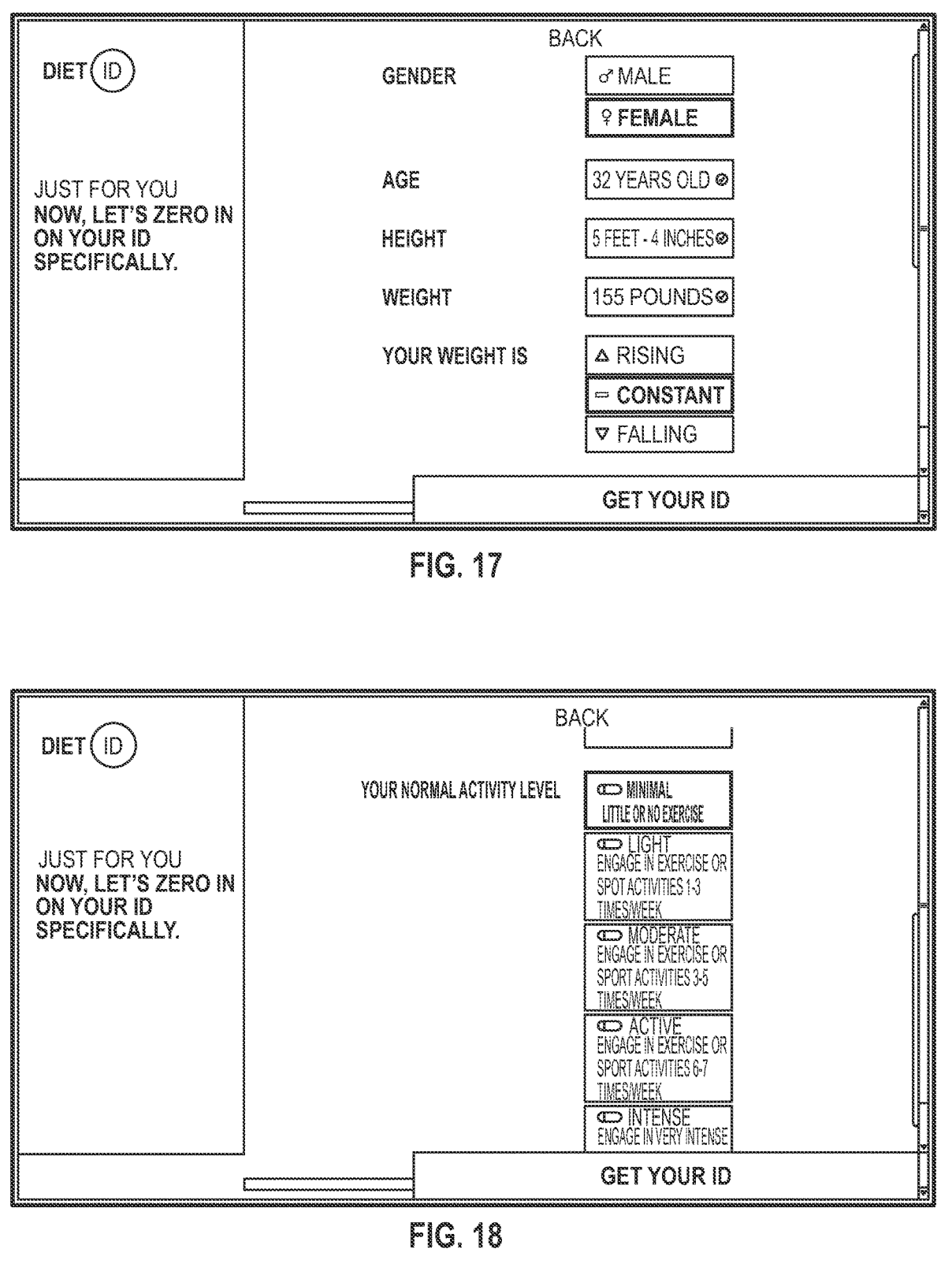
Figure 19:
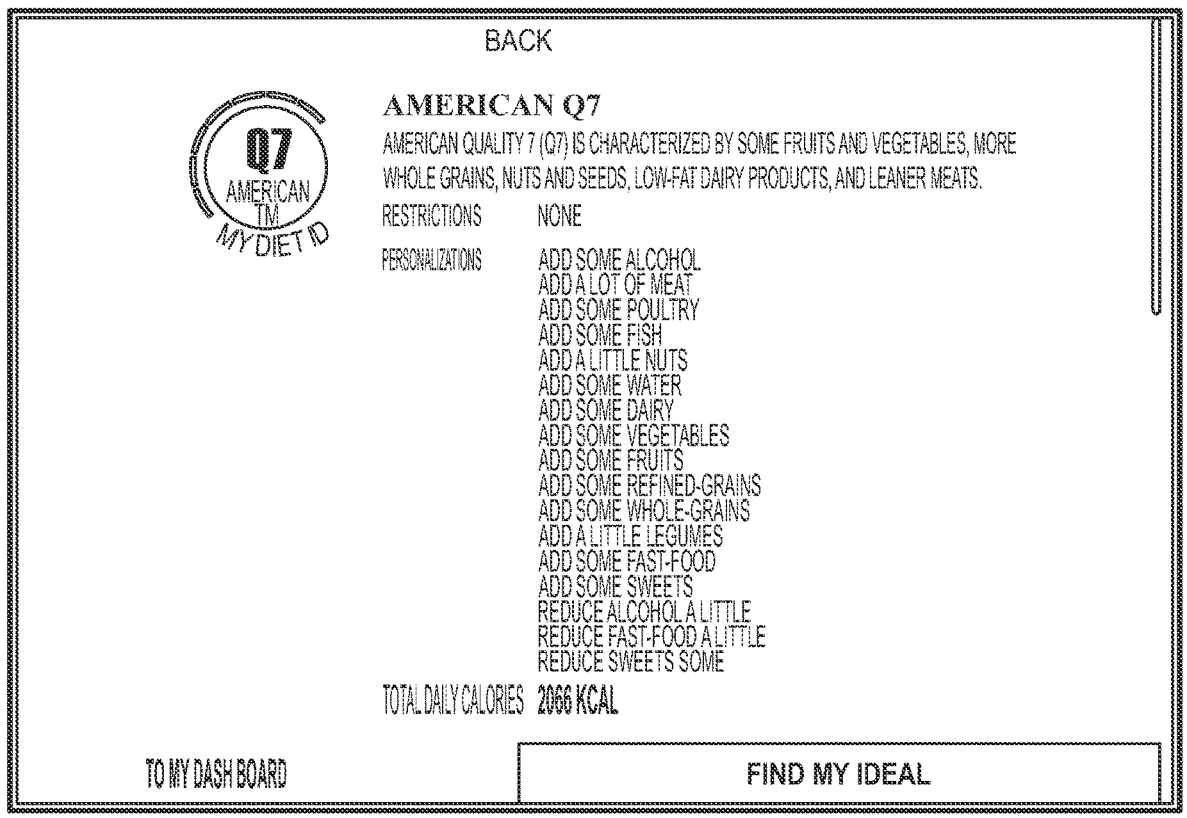
Figure 20:

FIG. 15 displays a composite image representing the current selected diet type N and diet quality level X of the user and invite the user to personal their diet. As shown in FIGS. 16 and 17, the diet quality level X can be personalized by adding, reducing, or removing certain elements from diet and/or composite image, including, for example, alcohol/wine, meat, poultry, seafood, etc. As an example, the user can interact with the composite image via a graphical user interface to modify the selected composite image with items that represent their preferences by, e.g., replacing foods or beverages in the composite image with alternatives, substitutes, replacements, etc. FIGS. 18 and 19 invite the user to input personal information, including gender, age, height, weight and activity level. FIG. 20 then displays a summary of the attribute of the personalized diet quality type N and level of diet quality X identified by the user.

Figure 21:
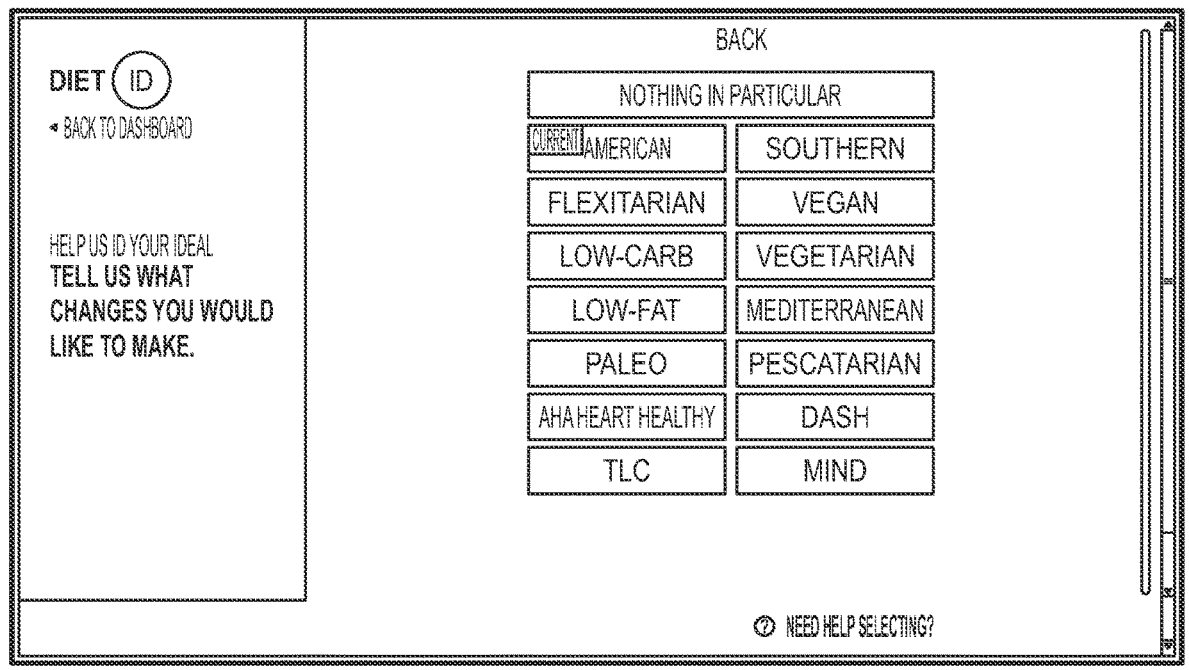
Figure 22:
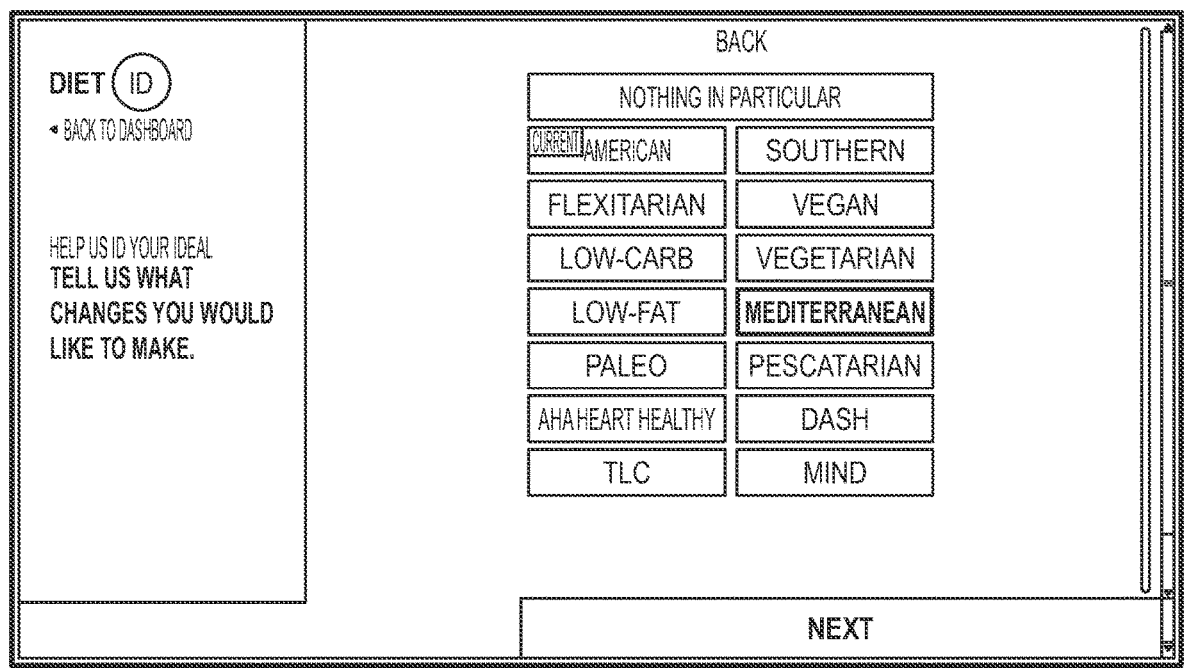
Figure 23:
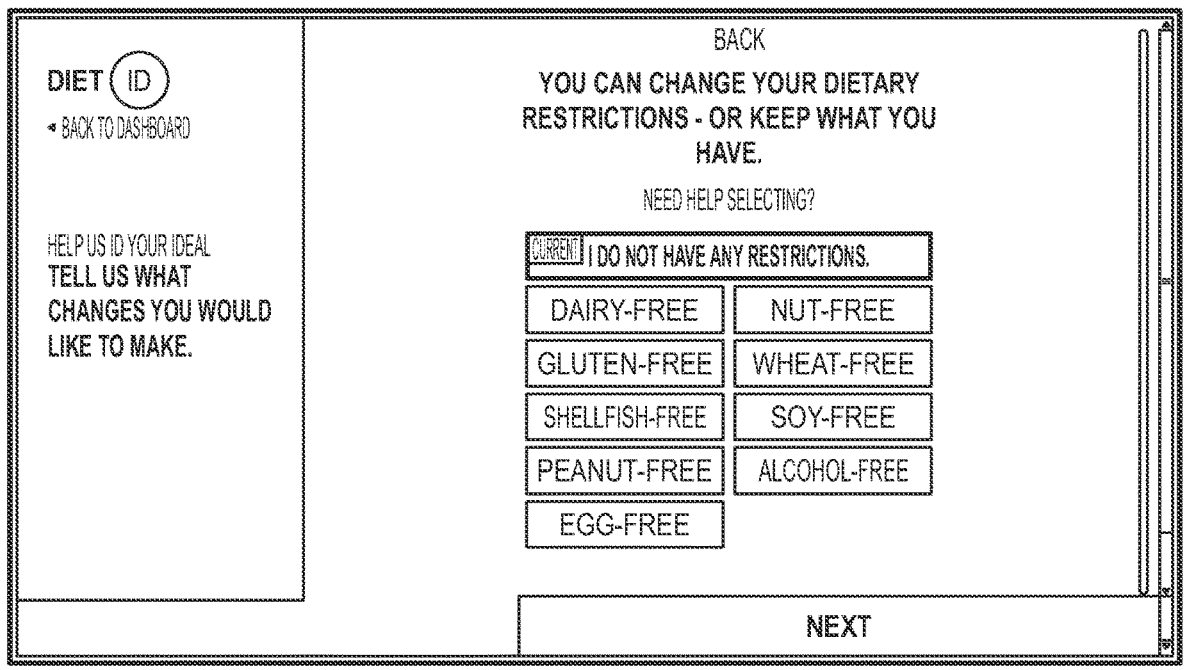
Figure 24:
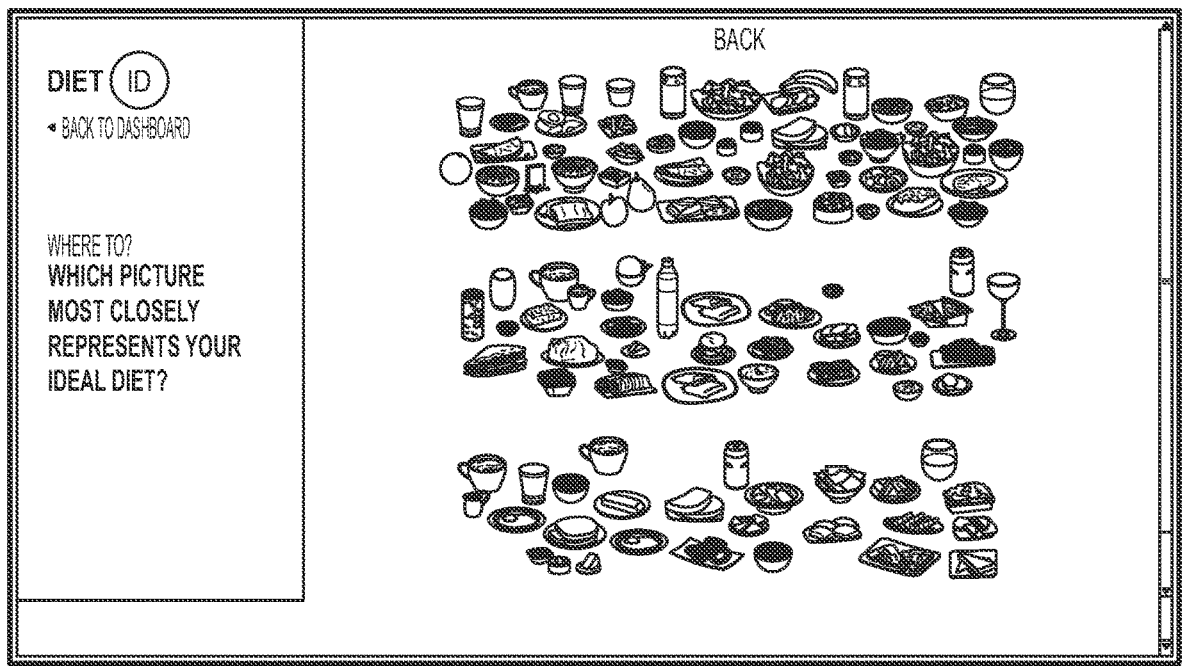
Figure 25:
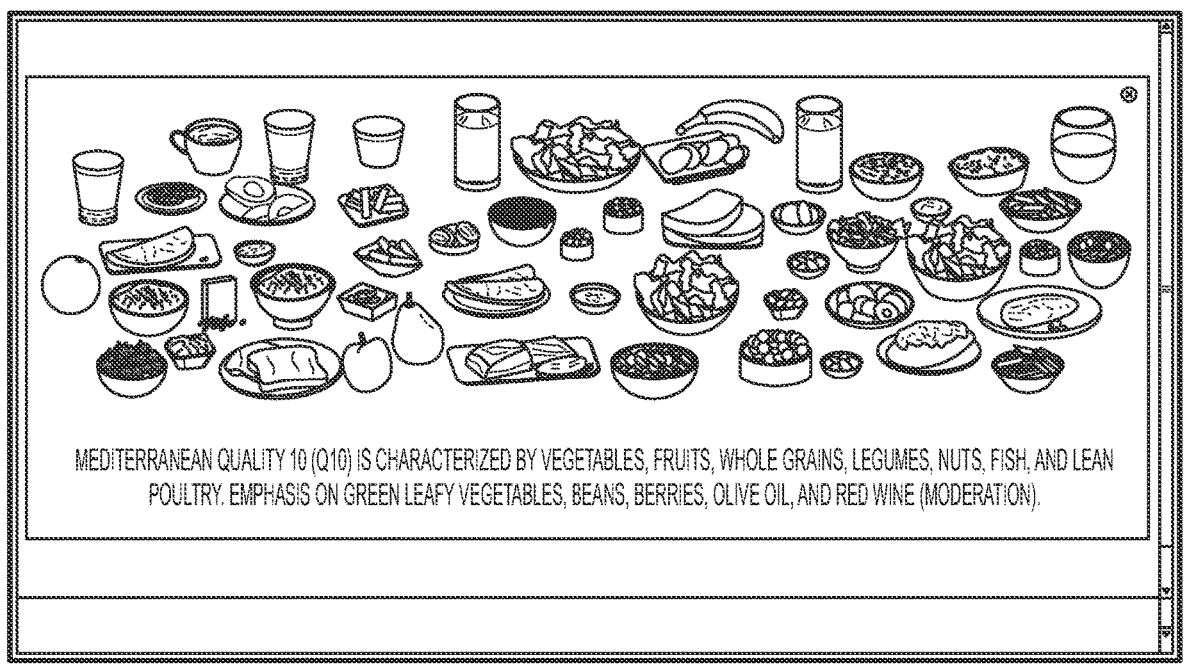
Figure 26:
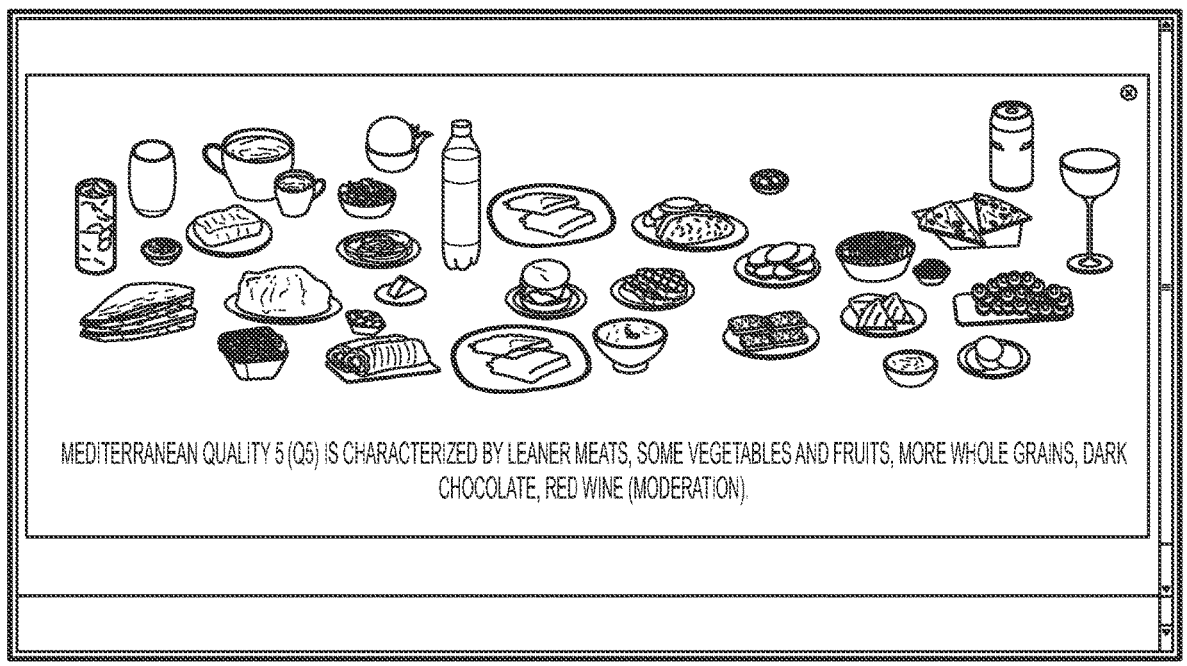
Figure 27:
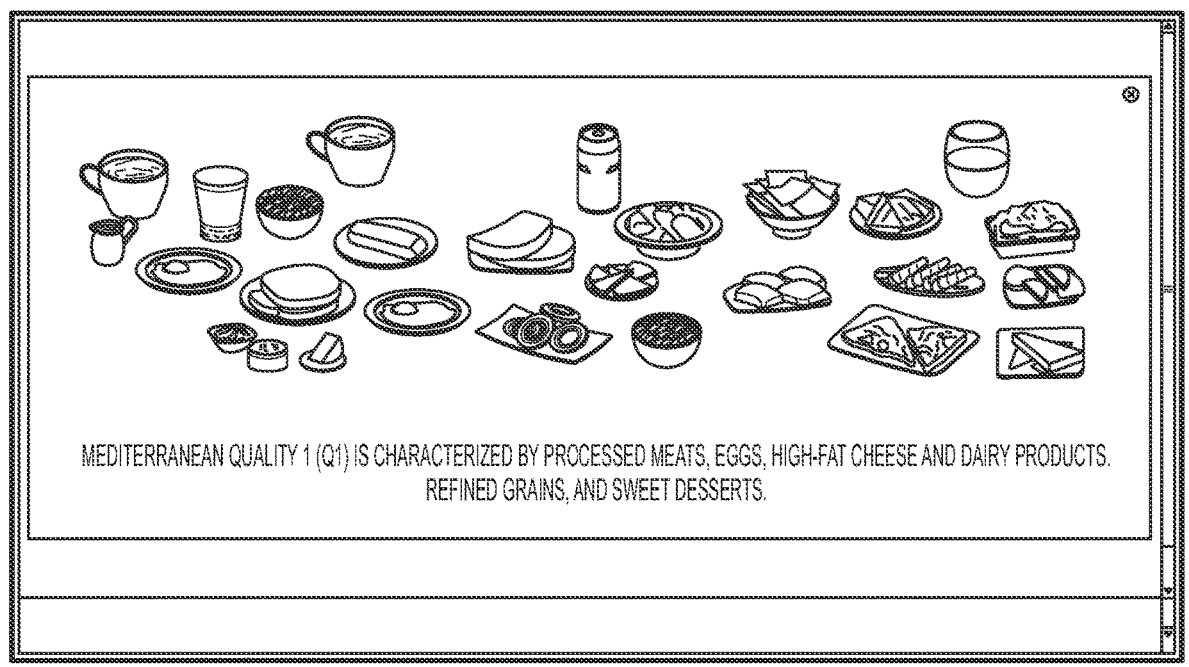
Figure 28:
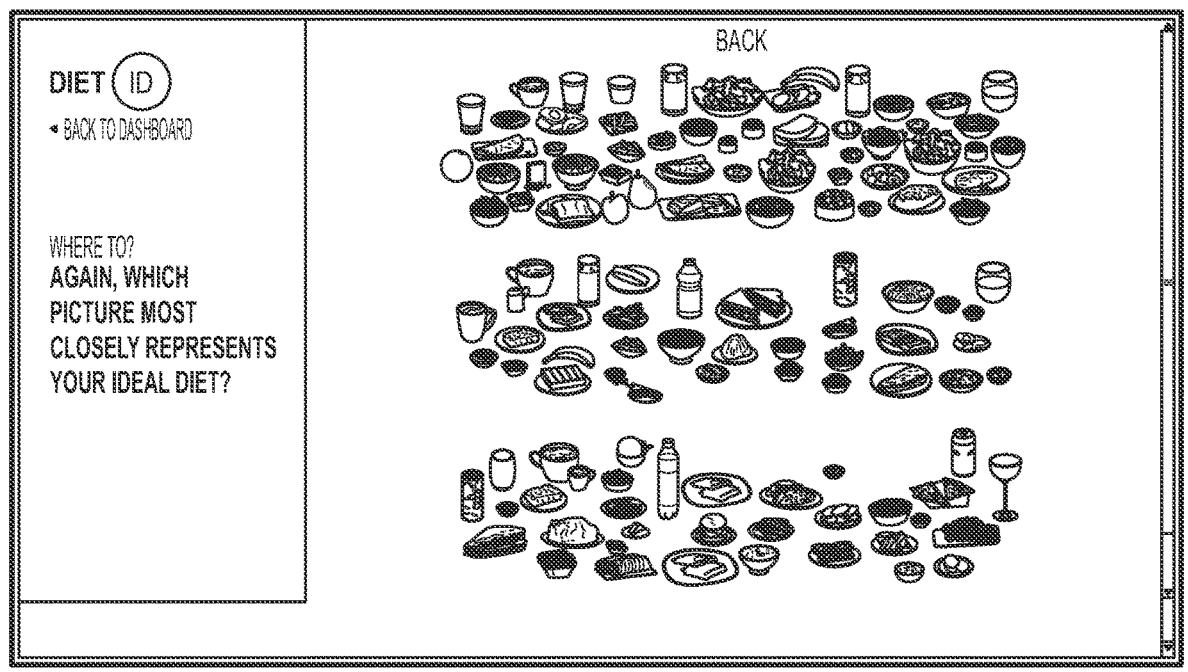
Figure 29:
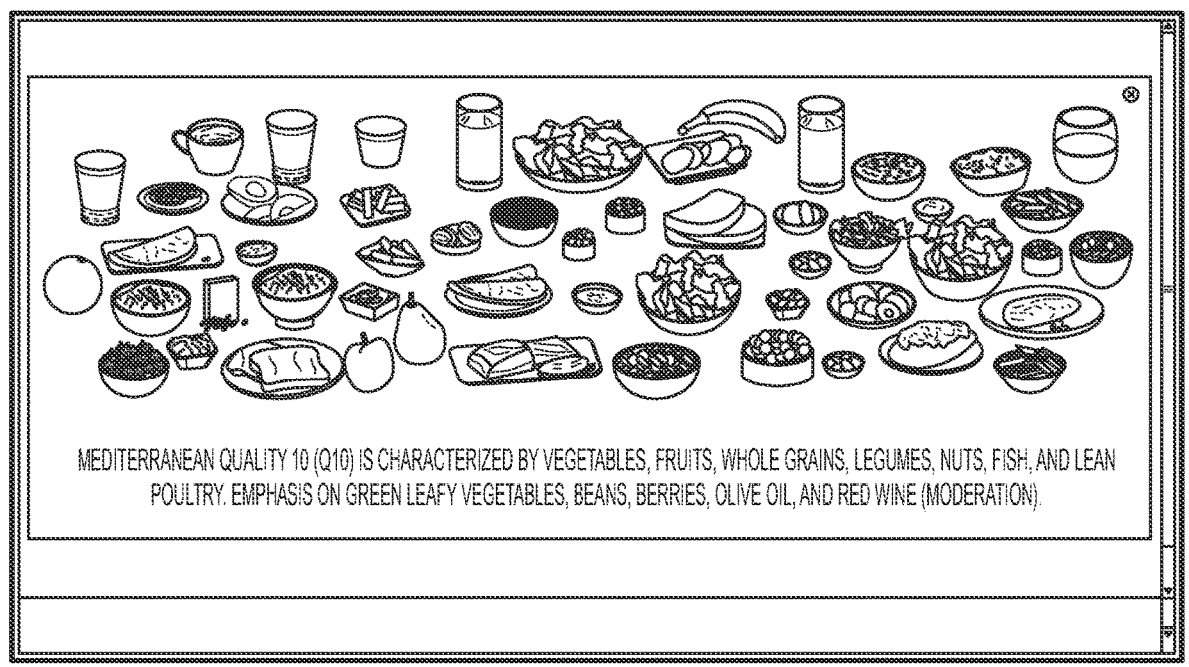
Figure 30:
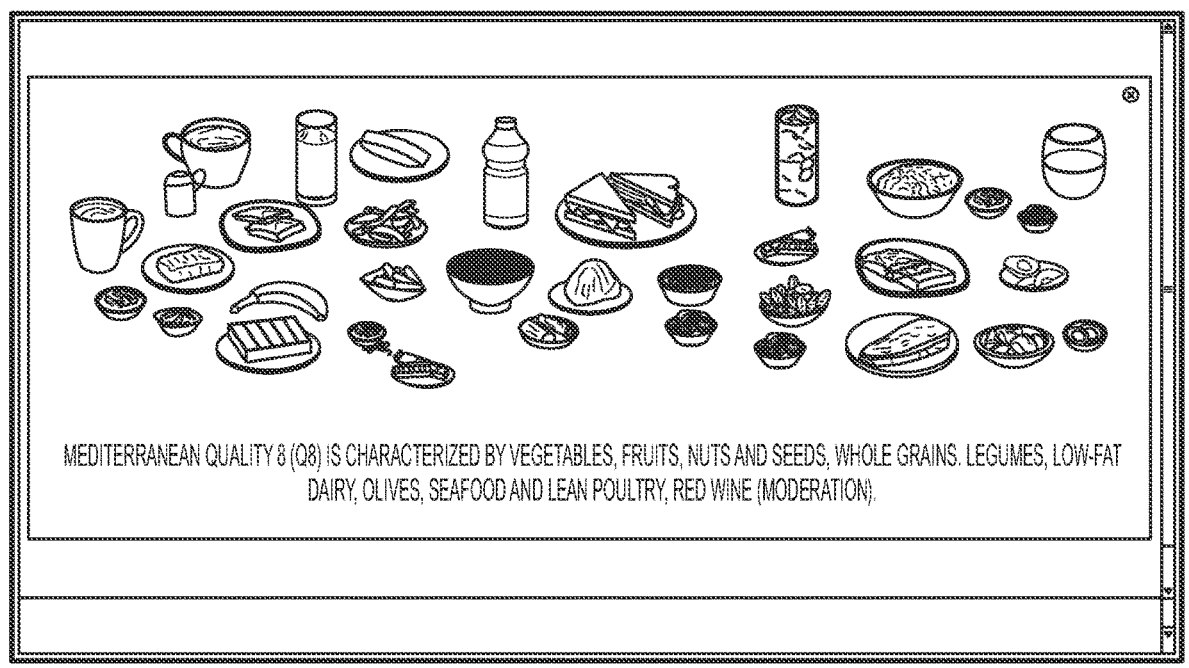
Figure 31:
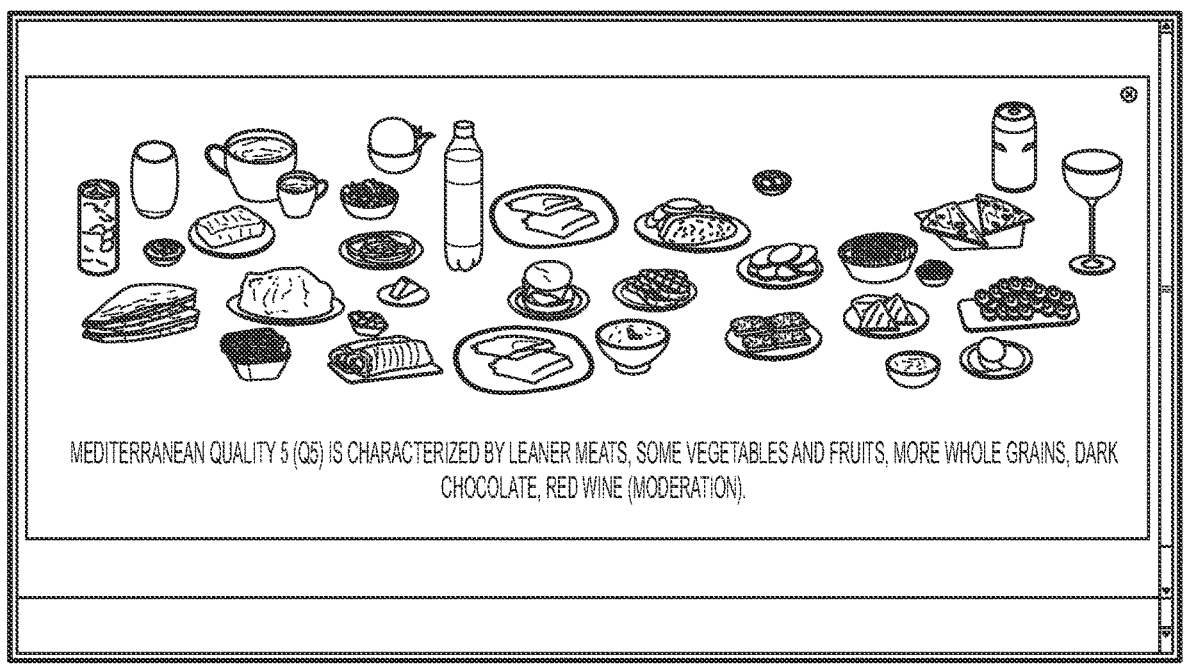
Figure 32:
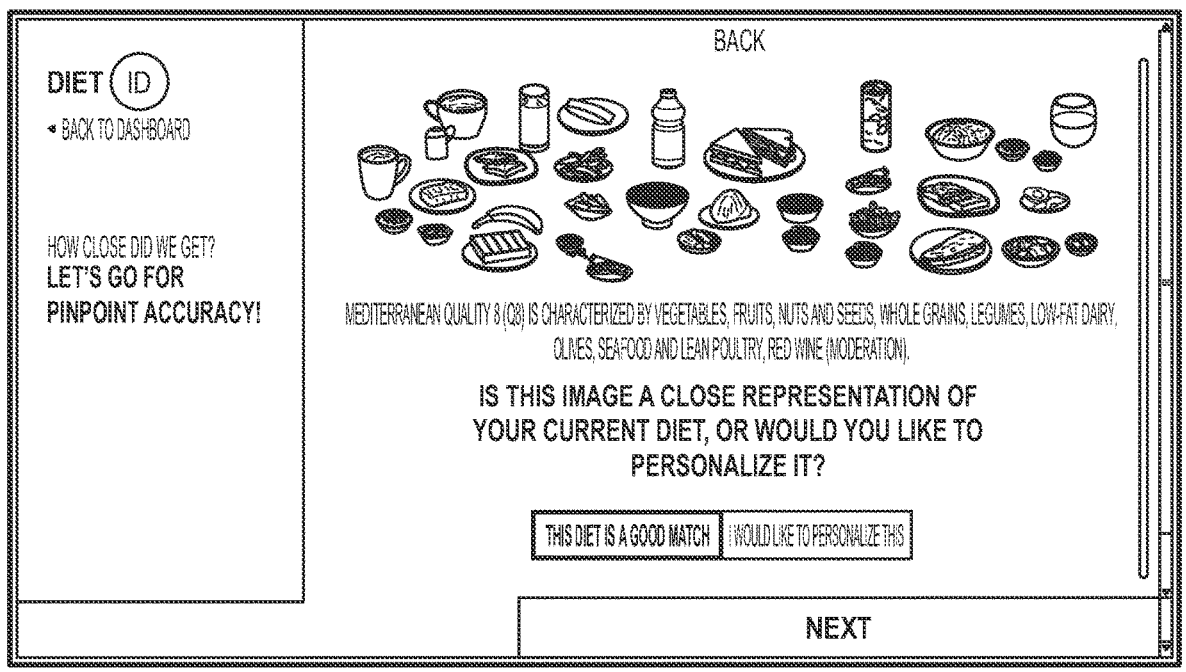
Figure 33:
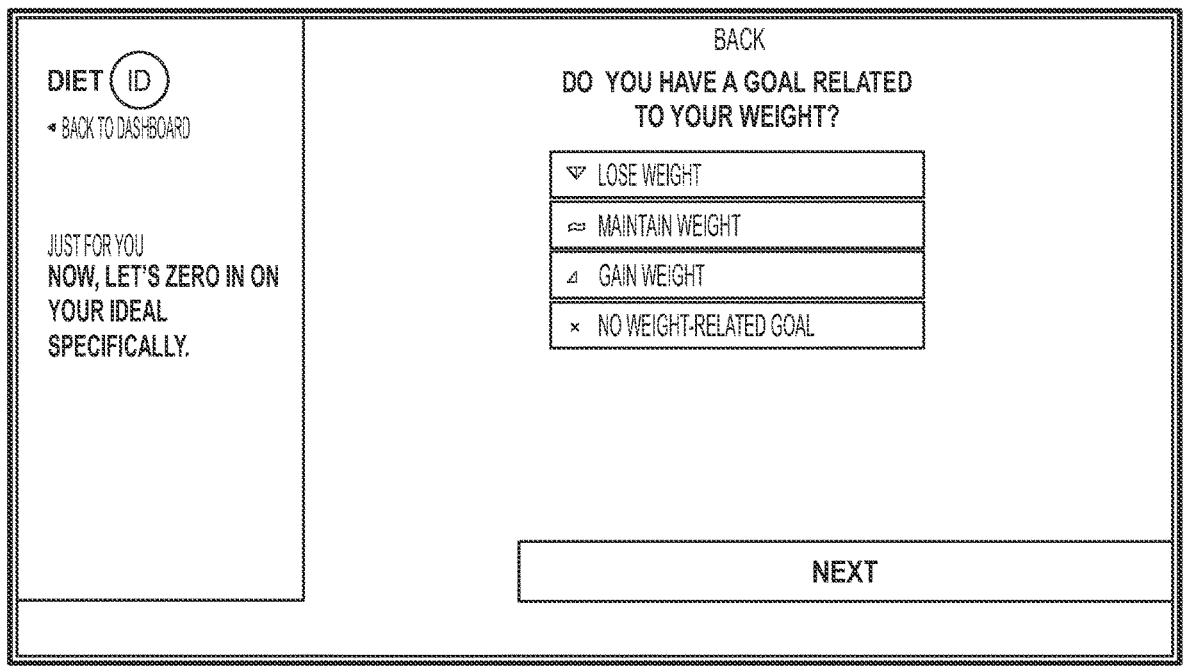
Figure 34:
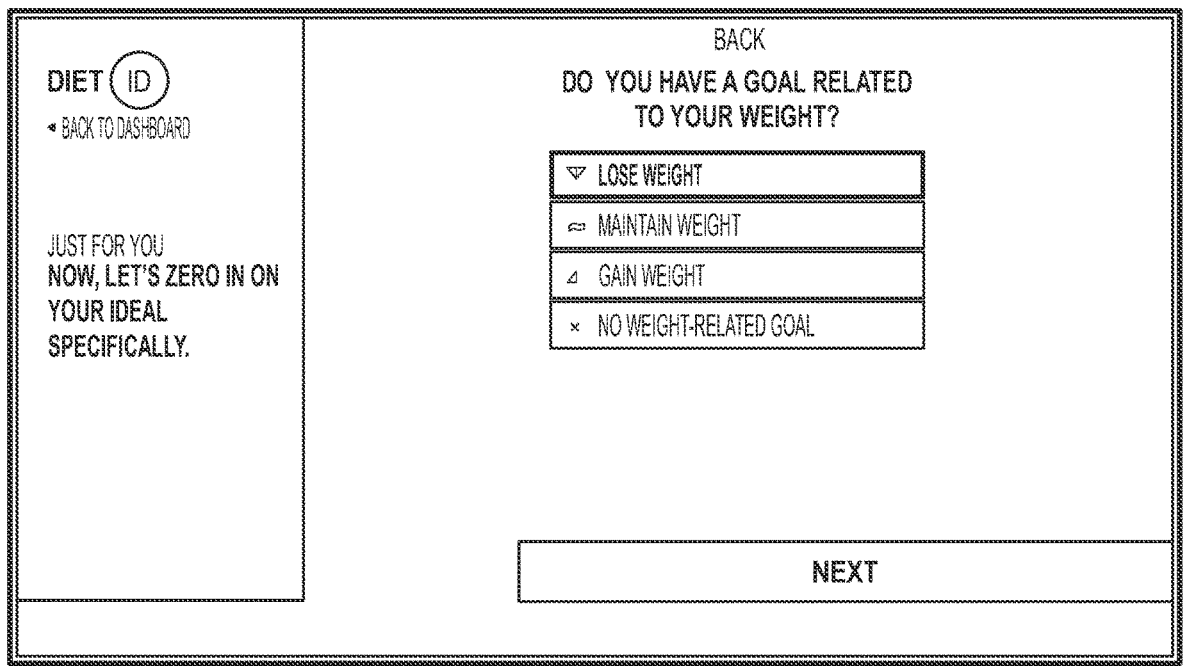
Figure 35:
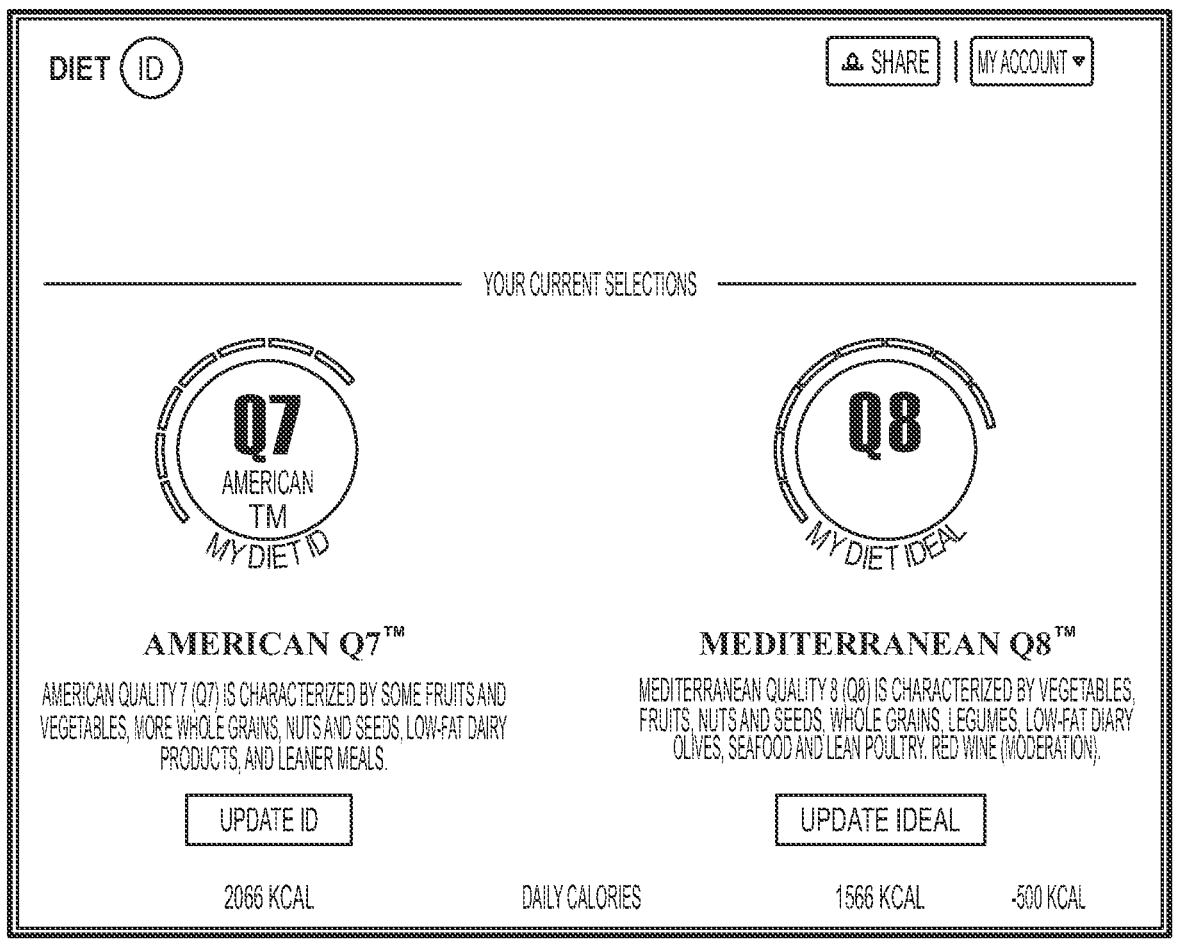

FIG. 21 then invites the user to find their ideal diet type N and or level of diet quality X. FIG. 22 invites the user to identify what changes they would like to make to their current diet type N and/or level of diet quality X and in FIG. 23, a user has chosen a "Mediterranean" diet as their updated or ideal diet type N. As shown in FIG. 24, the user can make changes to their dietary restrictions. FIG. 25 depicts another series of three composite images, each representing different levels of a Mediterranean diet type N and the user is invited to select the composite image that most represents their ideal diet. FIGS. 26-28 depict different diet quality levels X of the Mediterranean diet type N to allow the user additional information in making a determination. Upon selection of a composite image, the user is again invited to select a plurality of composite images as shown in FIG. 29 and FIGS. 30-32 again depict different diet quality levels X of a typical Mediterranean diet type N. As shown in FIG. 33, the user is again invited to personalize their diet. As shown in FIG. 34, the user can select a goal related to their diet and as shown in FIG. 33, the user has selected the goal of losing weight. FIG. 35 shows a dashboard of the user's current diet type N and level of diet quality X (i.e., American, Quality 7) and goal diet type N and level of diet quality X (i.e., Mediterranean, Quality 8) and FIG. 36 depicts a dashboard of nutrient levels of the two diet types and levels of diet quality, including daily calories, carbohydrates, total protein, total fat, etc.

Once the user has selected their goal or ideal diet type N and diet quality level X, information can be periodically sent to the user to assist them in a series of incremental steps in moving from their current diet to their ideal diet. In addition, this information can be changed and updated as needed or as desired by the user. Furthermore, and as set forth herein, these changes in diet may be desired for changes in level of diet quality X or diet type N, to minimize environmental impacts, or both.

It is also noted that FIGS. 3-36 depict a GUI in accordance with one aspect of the present invention, Further, the information displayed by the GUI can take many forms. For example, the composite images in the figures display a three-day menu, but the composite images may display foods arranged in different formats or may display food for a different number of days, Thus, the composite images may display an arrangement of foods for one day or two days or three days or four days of five days or seven day or I0 days, etc. In addition, the number of composite images displayed to the user for selection and comparison must be at least 2 but may be more.

Furthermore, the invention can take the form of a computer program product accessible from a computer-usable or computer-readable medium providing program code for use by or in connection with a computer or any instruction execution system. The software and/or computer program product can be implemented in the environment of FIG. 2. For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disc-read/write (CD-R/W) and DVD.

It should be understood, that while the steps have been described as occurring in a particular order, the invention contemplates that the steps may be performed in other orders, or one or more steps may not be employed, or may be performed more than once.

The invention claimed is:

1. A system implemented in hardware comprising:
a non-transitory computer usable medium having readable program code embodied in the medium;
a processor programmed to execute the program code to:
   a. display a menu of N diet types for selection by a user on a graphical user interface,
   b. display a first plurality of unique composite images of diet quality levels Xn, wherein each composite image contains images of foods in specific portions and depicts relative portions of ingredients, dishes and meals representative of the level of diet quality Xn of the N diet type selected by the user;
   c. display a different plurality of unique composite images of diet quality levels Xn upon selection by the user of one of the unique composite images in the first plurality of unique composite images, wherein one composite image of the level of diet quality Xn is the same as in the display of the first plurality of unique composite images and at least one composite image is different;
   d. display an input screen to allow the user to input personal information about the user on the graphical user interface;
   e. display an input screen to allow the user to input diet modification information on the graphical user interface; and
   f. calculate a user specific assessment of diet quality and type for the user and display the calculated user specific assessment of diet quality and type to the user on the graphical user interface.

2. The system of claim 1, further comprising a coaching tool, wherein the coaching tool is populated with a plurality of personalized coaching tips comprising discrete steps and changes to allow the user to modify their diet from one N diet type to a different N diet type and/or from one level of diet quality X to a different level of diet quality X, wherein the graphical user interface displays the personalized coaching tips to the user.

3. The system of claim 1, further comprising a diet tracking tool, wherein the graphical user interface displays an input screen to allow the user to change or update their diet type N, change or update their level of diet quality X, and the graphical user interface is capable of displaying changes in level of diet type N and level of diet quality X over time.

4. The system of claim 1, further comprising a navigation tool, wherein graphical user interface displays a personalized navigation route or navigation steps to the user to move the user stepwise from one level from one N diet type to a different N diet type and/or from one level of diet quality X to a different level of diet quality X, the personalized navigation route or steps being derived for the user based on a baseline diet and a goal diet derived from the inputs received via the graphical user interface.

5. The system of claim 1, wherein the input screen displays diet modification information comprising dietary preferences regarding specific ingredients, dishes, meals and/or foods and the input screen allows the user to input additions or subtractions in whole or in part of these specific ingredients, dishes, meals and/or foods.

6. The system of claim 5, wherein the dietary preferences comprise one or more of alcohol, meat, poultry, fish, nuts, water, dairy, vegetables, fruits, refined grains, whole grains, legumes, fast food, sweets, and alcohol.

7. The system of claim 1, wherein the diet modification information comprises dietary restrictions and the input screen allows the user to input the dietary restrictions.

8. The system of claim 7, wherein the dietary restrictions comprise one or more of dairy-free, gluten-free, shellfish-free, peanut-free, egg-free, nut-free, wheat-free, soy-free and alcohol-free.

9. The system of claim 1, wherein the personal information regarding the user comprises one or more of gender, age, height, weight, and activity level.

10. The system of claim 1, wherein each unique composite image depicts relative portions of foods, ingredients, and dishes for breakfast, lunch, dinner and snacks over a multi-day period, where the foods ingredients, and dishes exemplify a level of diet quality X of an N diet type.

* * * * *